(12) United States Patent
Greig et al.

(10) Patent No.: US 7,560,597 B2
(45) Date of Patent: Jul. 14, 2009

(54) 2',4'-DICHLORO-BIPHENYL-4-YL-HYDROXY-KETONES AND RELATED COMPOUNDS AND THEIR USE AS THERAPEUTIC AGENTS

(75) Inventors: Iain Robert Greig, Aberdeen (GB); Robert Jurgen van 't Hof, Edinburgh (GB); Stuart Hamilton Ralston, Edinburgh (GB)

(73) Assignee: The University Court of the University of Aberdeen, Aberdeen, Aberdeenshire (GB)

( * ) Notice: Subject to any disclaimer, the term of this patent is extended or adjusted under 35 U.S.C. 154(b) by 0 days.

(21) Appl. No.: 12/043,568

(22) Filed: Mar. 6, 2008

(65) Prior Publication Data
US 2008/0221220 A1 Sep. 11, 2008

Related U.S. Application Data

(60) Provisional application No. 60/905,619, filed on Mar. 8, 2007.

(51) Int. Cl.
*C07C 49/245* (2006.01)
*C07C 33/26* (2006.01)
*A61K 31/15* (2006.01)
*A61K 31/47* (2006.01)

(52) U.S. Cl. .................. 568/327; 568/807; 564/265; 514/640; 514/729

(58) Field of Classification Search .............. 568/327, 568/807; 564/265; 514/640, 729
See application file for complete search history.

(56) References Cited

FOREIGN PATENT DOCUMENTS

| JP | 2001352978 | * 12/2005 |
|---|---|---|
| WO | 2004/098582 | 11/2004 |

OTHER PUBLICATIONS

Baud, V. et al, "Signaling by proinflammatory cytokines: oligomerization of TRAF2 and TRAF6 is sufficient for JNK and IKK activation and target gene induction via an amino-terminal effector domain," Genes Dev. (1999) 13:1297-1308.
Brennan, F.M. et al., "Inhibitory effect of TNF alpha antibodies on synovial cell interleukin-1 production in rheumatoid arthritis," Lancet (1989) 334:244-247.
Brennan, F.M. et al., "Cytokines in autoimmunity," Curr. Opin. Immunol. (1996) 8:872-877.
Brennan, F.M. et al., "Enhanced expression of tumor necrosis factor receptor mRNA and protein in mononuclear cells isolated from rheumatoid arthritis synovial joints," Eur. J. Immunol. (1992) 22:1907-1912.
Corey, E.J. et al., "An efficient and catalytically enantioselective route to (S)-(-)-phenyloxirane," J. Org. Chem. (1988) 53:2861-2863.
Elliott, M.J. et al., "Randomised double-blind comparison of chimeric monoclonal antibody to tumour necrosis factor alpha (cA2) versus placebo in rheumatoid arthritis," Lancet (1994) 344:1105-1110.
Feldmann, M. et al., "TNF alpha as a therapeutic target in rheumatoid arthritis," Circ. Shock (1994) 43:179-184.
Feldmann, M. et al., "The role of TNF alpha and IL-1 in rheumatoid arthritis," Curr. Dir. Autoimmun. (2001) 3:188-199.
Feldmann, M. et al., "Rheumatoid arthritis," Cell (1996) 85:307-310.
Firestein, G.S. et al., "Invasive fibroblast-like synoviocytes in rheumatoid arthritis. Passive responders or transformed aggressors?" Arthritis Rheum. (1996) 39:1781-1790.
Firestein, G.S. et al., "Immunologic mechanisms in the pathogenesis of rheumatoid arthritis," J. Clin. Rheumatol. (2005) 11:S39-S44.

(Continued)

*Primary Examiner*—Sikarl A Witherspoon
(74) *Attorney, Agent, or Firm*—Michael Best & Friedrich LLP

(57) ABSTRACT

The present invention pertains generally to the field of therapeutic compounds, and more specifically to certain 2',4'-dichloro-biphenyl-4-yl-hydroxy-ketones and related compounds (collectively referred to herein as "DCBP compounds"), and more particularly to compounds selected from compounds of the following formula and pharmaceutically acceptable salts, solvates, and hydrates thereof:

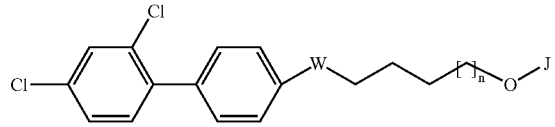

wherein: n is independently 1, 2, 3, or 4; W is independently —C(=O)—, —CH(OH)—, or —C(=NOR$^{OX}$)—; R$^{OX}$ is independently —H or C$_{1-3}$alkyl; J is independently: —H, —R$^{E1}$, —C(=O)—R$^{E2}$, —C(=O)—O—R$^{E3}$, —C(=O)—O—S(=O)$_2$OR$^{E4}$, —C(=O)—(CH$_2$)$_n$—C(=O)OR$^{E5}$, —C(=O)—(CH$_2$)$_n$—NR$^{NE1}$R$^{NE2}$, —C(=O)—(CH$_2$)$_n$—NR$^{NE3}$—C(=O)R$^{E6}$, —C(=O)—(CH$_2$)$_n$—C(=O)—NR$^{NE4}$R$^{NE5}$, or —P(=O)(OR$^{E7}$)(OR$^{E8}$); wherein each of R$^{E1}$, R$^{E2}$, R$^{E3}$, R$^{E4}$, R$^{E5}$, R$^{E6}$, and R$^{E7}$ is independently: —H, C$_{1-3}$alkyl, -Ph, or —CH$_2$-Ph. The present invention also pertains to pharmaceutical compositions comprising such compounds, and the use of such compounds and compositions, both in vitro and in vivo, in treatment and/or prevention, for example, of inflammation and/or joint destruction and/or bone loss; of disorders mediated by excessive and/or inappropriate and/or prolonged activation of the immune system; of, inflammatory and autoimmune disorders, for example, rheumatoid arthritis, psoriasis, psoriatic arthritis, inflammatory bowel disease, ankylosing spondylitis, and the like; of disorders associated with bone loss, such as bone loss associated with excessive osteoclast activation in rheumatoid arthritis, osteoporosis, cancer associated bone disease, Paget's disease and the like.

24 Claims, 2 Drawing Sheets

OTHER PUBLICATIONS

Firestein, G.S. et al, "Signal transduction and transcription factors in rheumatic disease," Arthritis Rheum. (1999) 42:609-621.

Gottlieb, A.B., "Psoriasis: Emerging Therapeutic Strategies," Nat. Rev. Drug Disc. (2005) 4:19-34.

Jimi, E. et al., "Selective inhibition of NF-kappa B blocks osteoclastogenesis and prevents inflammatory bone destruction in vivo," Nat. Med., (2004) 10:617-624.

Joosten, L.A. et al, "Anticytokine treatment of established type II collagen-induced arthritis in DBA/1 mice. A comparative study using anti-TNF alpha, anti-IL-1 alpha/beta, and IL-1Ra," Arthritis Rheum. (1996) 39:797-809.

Klareskog, L. et al, "A long-term, open-label trial of the safety and efficacy of etanercept (Enbrel) in patients with rheumatoid arthritis not treated with other disease-modifying antirheumatic drugs," Ann. Rheum. Dis. (2006) 65:1578-1584.

Klareskog, L. et al., "Mechanisms of disease: Genetic susceptibility and environmental triggers in the development of rheumatoid arthritis," Nat. Clin. Pract. Rheumatol. (2006) 2:425-433.

Korzenik, J.R. et al., "Evolving knowledge and therapy of inflammatory bowel disease," Nat. Rev. Drug Disc. (2006) 5:197-209.

Liu, Z.G., "Molecular mechanism of TNF signaling and beyond," Cell Res. (2005) 15:24-27.

Luckman, S.P. et al., "Heterocycle-containing bisphosphonates cause apoptosis and inhibit bone resorption by preventing protein prenylation: evidence from structure-activity relationships in J774 macrophages," J. Bone Miner. Res. (1998) 13:1668-1678.

McInnes, I.B. et al., "Targeting cytokines beyond tumor necrosis factor-alpha and interleukin-1 in rheumatoid arthritis," Curr. Pain Headache Rep. (2005) 9:405-411.

Mount, C. et al., "Rheumatoid arthritis market," Nat. Rev. Drug Disc. (2005) 4:11-12.

Nociari, M.N. et al., "A Novel one-step, highly sensitive fluorimetric assay to evaluate cell-mediated cytotoxicity," Journal of Immunological Methods (1998) 213:157-167.

Ramachandran, P.V. et al., "Chiral synthesis via organoboranes. 40. Selective reductions. 55. A simple one-pot synthesis of the enantiomers of (trifluoromethyl)oxirane. A general synthesis in high optical purities of alpha trifluoromethyl secondary alcohols via the ring-cleavage reactions of the epoxide," J. Org. Chem. (1995) 60:41-46.

Roodman, G.D., "Regulation of osteoclast differentiation," Ann. N. Y. Acad. Sci. (2006) 1068:100-109.

Smolen, J.S. et al., "Therapeutic Strategies for Rheumatoid Arthritis," Nat. Rev. Drug Disc. (2003) 2:473-488.

Tanaka, S. et al., "Signal transduction pathways regulating osteoclast differentiation and function," J. Bone Miner. Metab. (2003) 21:123-133.

Van Den Berg, W.B., "Is there a rationale for combined TNF and IL-1 blocking in arthritis?" Clin. Exp. Rheumatol. (2002) 20:S21-S25.

Van Den Berg, W.B. et al., "Pathogenesis of joint damage in rheumatoid arthritis: evidence of a dominant role for interleukin-I," Baillieres Best Pract. Res. Clin. Rheumatol. (1999) 13:577-597.

Weissmann, G., "The pathogenesis of rheumatoid arthritis," Bull. Hosp. Jt. Dis. (2006) 64:12-15.

Ziff, M., "Rheumatoid arthritis—it's present and future," J. Rheumatol. (1990) 17:127-133.

Extract from prosecution file for European Patent Application No. 04 731 404.2: letter dated Mar. 13, 2006—"Response to Communication pursuant to Rules 109 and 110 EPC" (7 pages).

* cited by examiner

US 7,560,597 B2

2',4'-DICHLORO-BIPHENYL-4-YL-HYDROXY-KETONES AND RELATED COMPOUNDS AND THEIR USE AS THERAPEUTIC AGENTS

RELATED APPLICATION

This application is related to, and claims priority benefit of, U.S. provisional patent application No. 60/905,619 filed 8 Mar. 2007, the contents of which are incorporated herein in their entirety.

TECHNICAL FIELD

The present invention pertains generally to the field of therapeutic compounds, and more specifically to certain 2',4'-dichloro-biphenyl-4-yl-hydroxy-ketones and related compounds (collectively referred to herein as "DCBP compounds"). The present invention also pertains to pharmaceutical compositions comprising such compounds, and the use of such compounds and compositions, both in vitro and in vivo, in treatment and/or prevention, for example, of inflammation and/or joint destruction and/or bone loss; of disorders mediated by excessive and/or inappropriate and/or prolonged activation of the immune system; of inflammatory and autoimmune disorders, for example, rheumatoid arthritis, psoriasis, psoriatic arthritis, inflammatory bowel disease, ankylosing spondylitis, and the like; of disorders associated with bone loss, such as bone loss associated with excessive osteoclast activation in rheumatoid arthritis, osteoporosis, cancer associated bone disease, Paget's disease and the like.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Rheumatoid Arthritis

Rheumatoid arthritis (RA) is a chronic inflammatory disease characterised by painful swelling, stiffness, loss of movement and the destruction of cartilage and bone. RA is characterised by an inflammation of the synovial lining of multiple joints and commonly affects the joints of the wrist and hands and may also affect the elbows, shoulders, hips, neck and knees; the ultimate hallmark of RA is joint destruction. RA is a common disease, estimated to affect up to 1% of adults in the developed world, with women more than twice as likely to be affected and over 30% of patients likely to become severely disabled within 20 years (see, e.g., Feldmann et al., 2006). RA is one of the most important causes of disability in the western world and is associated with a significant reduction in quality of life as well as increased mortality if left untreated. The disease can start at any age, with individuals aged between 40 and 70 most commonly affected.

The exact cause of RA remains unclear, but is highly complex and may involve the combination of a number of factors which lead to the development of autoantibodies, formation of immune complexes, production of pro-inflammatory cytokines, angiogenesis and eventual bone and cartilage loss (see, e.g., Klareskog et al, 2006; Ziff et al, 1990; Weissmann et al, 2006; Firestein et al, 2005). These factors include an abnormal immune response caused by reduced self tolerance or a biological trigger such as reaction to environmental factors, infectious agents, or hormonal stimulus (see, e.g., Klareskog et al, 2006); antibodies to the Fc fragment of IgG, known as rheumatoid factor, are present in 60-80% of adults with RA (see, e.g., Weissmann et al, 2006) but it is not known whether this is factor is responsible for initiating the inflammatory cascade or are generated at a later stage and propagate the process (see, e.g., Weissmann et al, 2006); there is also a notable genetic predisposition to the disease, as shown by the presence of HLA-DR4 antibody in 70% of patients (see, e.g., Klareskog et al, 2006).

At the cellular level, development of RA usually commences with T-cells infiltrating the synovial membrane lining the affected joint; this then leads to the activation of macrophages, monocytes and synovial fibroblasts (see, e.g., Firestein, 1996) by way of cell-cell contact and release of various cytokines, including TNFα and IL-1 (see, e.g., Feldmann, 1996). Activation of these cells leads to the overproduction of a range of pro-inflammatory cytokines of which the most important are TNFα, IL-1 and IL-6 (see, e.g., Brennan et al, 1996; McInnes et al, 2005). These pro-inflammatory cytokines are then instrumental in orchestrating several complex signal transduction cascades, including the NFκB, MAPK and Jak/STAT pathways (see, e.g., Firestein et al, 1999) which lead to the induction of genes coding for various products which propagate the inflammatory response and also promote tissue destruction. These products include tissue degrading enzymes such as collagenases, matrix metalloproteases, cathepsins, and other pro-inflammatory factors such as selectins, integrins, leukotrienes, prostaglandins, chemokines, and other cytokines. Furthermore, TNFα and IL-1 also induce RANKL expression.

RANKL is an essential factor for the generation of osteoclasts (see, e.g., Tanaka et al, 2003; Roodman, 2006), and upregulated RANKL-production leads to increased osteoclasts differentiation and ultimately bone destruction (see, e.g., Tanaka et al, 2003; Roodman, 2006). The inflammatory response leads to the accumulation of many leukocytes and immune factors populations within the affected joint and also to hyperplasia of the Type-A and Type-B synovicytes (see, e.g., Firestein et al, 2005), leading to thickening and vascularisation of the synovium into a destructive and aggressive tissue known as a pannus. The pannus contains both osteoclasts which destroy bone, and metalloproteases which continue the destruction of cartilage.

Treatment of Rheumatoid Arthritis

Early therapies for RA focussed on controlling the symptoms of the disease, mainly by reduction of inflammation, rather than retarding disease progression. These drugs included NSAIDs such as aspirin, diclofenac and naproxen and, until recently, the COX-2 selective drugs Celebrex® and Vioxx® were also widely used. Inflammation was further controlled by glucocorticoids, and their combination with NSAIDs provided reasonably effective short-term control of the inflammation. More recently, a more aggressive approach to treating RA has been introduced starting at disease onset, using so-called disease-modifying anti-rheumatic drugs (DMARDs) which act to slow or even prevent disease progression. These include a number of older drugs, including gold salts; sulfasalazine; antimalarials such as hydroxychloroquine; D-penicillamine; immunosuppressants such as mycophenolic acid, azathioprine, cyclosporine A, tacrolimus and sirolimus; minocycline; leflunomide; and most importantly, methotrexate (see, e.g., Smolen et al, 2003).

Methotrexate is now the gold-standard therapy for clinical trial comparisons, and is generally used in combination with newer therapies. It is effective in most patients but, in common with all of the above agents, has significant gastrointestinal side effects which lead to roughly 50% of patients eventually having to cease treatment with methotrexate (see, e.g., Mount et al, 2005). A further drawback of these older DMARDs is the length of time taken for the drug to start acting, ranging from weeks with methoxtrexate, to months with gold salts. Whilst full remissions only occur in about a quarter of patients, for those showing no effect it is not generally possible to stop therapy without suffering the risk of a more violent disease rebound (see, e.g., Smolen et al, 2003). In recent years, the treatment of RA has been revolutionised by the advent of biological agents which target specific inflammatory pathways. The first and most important of these are the anti-tumour necrosis factor (anti-TNF) agents (see, e.g., Elliott et al, 1994).

The Role of TNFα in RA

As discussed above, the TNF superfamily of receptors and ligands plays a key role in the causation of inflammation and associated local and systemic bone loss. TNFα production within the joint may in fact play the pivotal role in orchestrating the production of other factors which leads to the persistence of inflammation and tissue damage (see, e.g., Feldmann et al, 2001; Brennan et al, 1999; Brennan, 1992). The importance of TNFα in RA is highlighted by the finding that antibodies blocking TNF can prevent inflammation in animal models of RA, and that anti-TNF therapy is currently the most effective treatment for RA (see, e.g., Elliott et al, 1994; Feldmann et al, 1994; Joosten et al 1996, Klareskog et al, 2006). However, there is evidence that there are some TNF-independent effects of IL-1 in RA, most notably bone destruction (see, e.g., van den Berg et al, 1999; van den Berg et al, 2002).

TNF is a cytokine that affects many different functions, including the alteration of tissue remodelling, changes to the permeability of the epithelial cell barrier, activation of macrophages, up-regulation of adhesion molecules, recruitment of other immune response effectors and, most importantly in RA, it instigates the signalling cascade which leads to the activation of the transcription factors NFκB and AP-1 (see, e.g., Liu, 2005; Baud et al, 1999). Binding of TNF and IL-1 to their respective receptors leads to the recruitment of downstream signal transducers called TRAFs. Further kinases are recruited by the TRAFs, and the resulting kinase complex activates the Map-kinase pathway, ultimately leading to activation of AP-1, and the phosphorylation of IκB kinase. IκB is the inhibitor of NFκB, which acts by preventing translocation of NFκB to the nucleus. Phosphorylation of IκB by IκB kinase leads to degradation of IκB. Once IκB has been degraded, NFκB migrates to the nucleus, where it promotes transcription of anti-apoptotic genes, which promote survival of T and B-cells, thereby prolonging the immune response. This prolongation of the inflammatory response is central to the chronic nature of RA. The importance of NFκB activation is demonstrated by the fact that inhibition of NFκB activity by inhibitory peptides can prevent arthritis in animal models of RA (see, e.g., Jimi et al, 2004).

Anti-TNFα Therapy

Anti-TNFα therapy represents the market-leading therapies for RA, and is performed either with neutralising antibodies such as infliximab (Remicade® J&J and Schering Plough) and adalimumab (Humira®, Abbott) or decoy receptors such as etanercept (Enbrel® Amgen and Wyeth), both which represent validated and highly effective treatments for RA. Anti-TNF biologicals are already licensed for RA, Crohn's disease, and psoriasis. A number of other inflammatory and autoimmune disorders are also being investigated as potential targets. Other approaches to blocking the action of TNF include the pegylated anti-TNF fragment certolizumab (Cimzia®, UCB); inhibition of proximal signalling intermediates such as MAP kinase; interference with the synthesis of TNF via inhibition of TNFα converting enzyme (TACE); and inhibition of the metalloproteases responsible for cleaving TNF from the cell surface (see, e.g., Smolen et al, 2003; Mount et al, 2005).

Other Inhibitors of NFκB Activation

As described above, the binding of IL-1 and RANKL to their receptors also initiates a signalling cascade, which eventually leads to the activation of NFκB and subsequent inflammatory response. The efficacy of inhibitors of these ligands has been validated by the use of the IL-1 receptor antagonist anakinra (Kineret® Amgen) for the treatment of RA, and the progression of the monoclonal antibody against RANKL AMG-162 (Denosumab® Amgen) through to phase III clinical trials for osteoporosis (it is also in clinical trials for RA and psoriasis).

Other Common Inflammatory Diseases Mediated by TNFα

There are several other common inflammatory diseases in which TNFα has been shown to play a major role and in which TNFα inhibitors have found therapeutic use. These include inflammatory bowel disease (IBD) and psoriasis.

IBD is an inflammatory disorder of the gut affecting about 0.25% of the population in the western world, of which the two main forms are: ulcerative colitis (UC), in which the lining of the colon becomes inflamed and ulcerated; and Crohn's disease (CD), which can occur anywhere within the gastrointestinal tract, but most often the ileum, and commonly involves inflammation of the entire gut wall. Common symptoms of IBD are bloody diarrhea and abdominal pain.

Psoriasis is an inflammatory response of the skin affecting 1-3% of the population in the western world. The disease is characterised by raised, red, scaly plaques on the skin, which may be itchy and also cause significant psychological distress by their unsightly nature. A further complication of psoriasis is the development of psoriatic arthritis, an inflammatory arthritis of the joints, in up to 40% of patients, which develops on average 10 years after the first symptoms of skin disease are seen (see, e.g., Gottlieb, 2005).

As with RA, the etiology of IBD and psoriasis are unknown and may involve a complex combination of infectious agents, environmental, and genetic factors, generating an inappropriate and prolonged inflammatory response.

Treatment of IBD and psoriasis has followed a similar pattern to that of RA, with the past use of immunoregulatory agents such as NSAIDs, methotrexate, cyclosporine, steroids, and antimetabolites such as 6-mercaptopurine for IBD (see, e.g., Korzenik et al, 2006) and methotrexate and cyclosporine for psoriasis (see, e.g., Gottlieb, 2005). The treatment of both has been revolutionised by the advent of biological agents, in particular those which block TNFα signalling. Etanercept is licensed for the treatment of psoriasis and psoriatic arthritis; both infliximab and adalimumab are licensed for psoriatic arthritis and IBD and are in late stage clinical trials for psoriasis.

Common Bone Diseases

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis may also arise in association with inflammatory diseases such as rheumatoid arthritis, endocrine diseases such as thyrotoxicosis, and with certain drug treatments such as treatment with glucocorticoids. However one of the most important factors in the pathogenesis of osteoporosis is heredity.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

Bone involvement is a feature of many types of cancer. Cancer-associated bone disease can be manifest by the occurrence of hypercalcaemia or the development of osteolytic and/or ostesclerotic metastases. Increased osteoclastic bone resorption plays a key role in the pathogenesis of both conditions. Whilst almost any cancer can be complicated by bone metastases, the most common causes are multiple myeloma, breast carcinoma, and prostate carcinoma. The most common tumours associated with hypercalcaemia are multiple myeloma, breast carcinoma, and lung carcinoma.

RANKL signalling has been shown to play a major role in osteoclast over-activity and a consequent increase in bone loss (see, e.g., Tanaka et al, 2003; Roodman, 2006). The use of drugs which affect this pathway has been validated by the progression through to phase III/II clinical trials of the monoclonal antibody against RANKL AMG-162 (Denosumab® Amgen) for the treatment of osteoporosis/multiple myeloma.

As described previously, bone loss also plays a major role in the pathophysiology of rheumatoid arthritis and drugs which prevent activation of the signalling pathways described (e.g. TNFα blockers) are also able to prevent this bone loss.

Agents that Prevent Inflammation and/or Bone Loss

The inventors have identified a new class of compounds which, for example, prevent inflammation and/or bone loss, and thus may be used in the treatment of diseases with an inflammatory or autoimmune component, including, for example, rheumatoid arthritis, inflammatory bowel disease, psoriasis, and psoriatic arthritis; as well as diseases which involve bone loss, including, for example, bone loss associated with rheumatoid arthritis, osteoporosis, Paget's disease of bone, and multiple myeloma.

Without wishing to be bound by any particular theory, the inventors believe that this action may be via a mechanism that involves blocking TNFα and/or IL-1 and/or RANKL-signalling.

Biphenyl Ketones

Greig et al, 2003, describes a broad class of biphenyl ketones as anti-resorptive agents for the treatment of bone diseases. The present inventors have identified a much narrower subclass of biphenyl ketones, specifically, certain 2',4'-dichloro-biphenyl-4-yl-hydroxy-ketones and related compounds, as defined herein, that have surprising and unexpected properties.

Specifically, the representative compound, 1-(2',4'-dichloro-biphenyl-4-yl)-6-hydroxy-hexan-1-one (ABD328), is orally active, fully prevents bone loss in the mouse ovariectomy model, and also prevents inflammation in the collagen-induced arthritis model.

Consequently, compounds within the narrower subclass of biphenyl ketones described herein (and in particular, ABD328) have the potential to be orally active agents for the treatment of inflammatory diseases and/or for the treatment and/or prevention of bone loss.

SUMMARY OF THE INVENTION

One aspect of the invention pertains to certain 2',4'-dichloro-biphenyl-4-yl-hydroxy-ketones and related compounds (collectively referred to herein as "DCBP compounds"), as described herein.

Another aspect of the invention pertains to a composition comprising a DCBP compound as described herein and a pharmaceutically acceptable carrier or diluent.

Another aspect of the invention pertains to a method of inhibiting an inflammatory response, in vitro or in vivo, comprising contacting an immune system component with an effective amount of a DCBP compound, as described herein.

Another aspect of the invention pertains to a method of inhibiting cellular and/or molecular pathways leading to joint destruction, in vitro or in vivo, comprising contacting cells associated with an immune response with a therapeutically-effective amount of a DCBP compound, as described herein.

Another aspect of the invention pertains to a method of inhibiting osteoclast survival, formation, and/or activity, in vitro or in vivo, comprising contacting an osteoclast with an effective amount of a DCBP compound, as described herein.

Another aspect of the invention pertains to a method of inhibiting bone resorption, in vitro or in vivo, comprising contacting cells in the bone microenvironment with a therapeutically-effective amount of a DCBP compound, as described herein.

Another aspect of the present invention pertains to a method of treatment and/or prevention comprising administering to a subject in need of treatment and/or prevention a therapeutically-effective amount of a DCBP compound, as described herein, preferably in the form of a pharmaceutical composition.

In one embodiment, the administering is orally administering.

Another aspect of the present invention pertains to a DCBP compound as described herein for use in a method of treatment and/or prevention of the human or animal body by therapy.

Another aspect of the present invention pertains to use of a DCBP compound, as described herein, in the manufacture of a medicament for use in treatment and/or prevention.

In one embodiment, the treatment and/or prevention is treatment and/or prevention of inflammation and/or joint destruction and/or bone loss.

In one embodiment, the treatment and/or prevention is treatment and/or prevention of disorders mediated by excessive and/or inappropriate and/or prolonged activation of the immune system.

In one embodiment, the treatment and/or prevention is treatment and/or prevention of inflammatory and autoimmune disorders, for example, rheumatoid arthritis, psoriasis, psoriatic arthritis, inflammatory bowel disease, ankylosing spondylitis, and the like.

In one embodiment, the treatment and/or prevention is treatment and/or prevention of disorders associated with bone loss, such as bone loss associated with excessive osteoclast activation in rheumatoid arthritis, osteoporosis, cancer associated bone disease, Paget's disease and the like.

Another aspect of the present invention pertains to a kit comprising (a) a DCBP compound, as described herein, preferably provided as a pharmaceutical composition and in a suitable container and/or with suitable packaging; and (b) instructions for use, for example, written instructions on how to administer the DCBP compound.

Another aspect of the present invention pertains to DCBP compounds obtainable by a method of synthesis as described herein, or a method comprising a method of synthesis as described herein.

Another aspect of the present invention pertains to DCBP compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
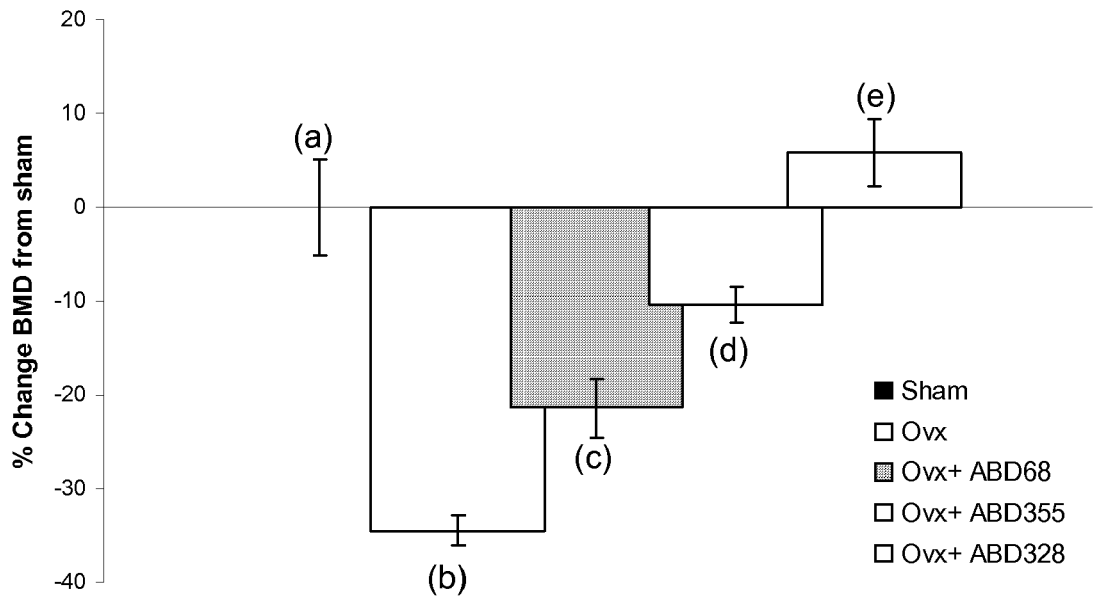
FIG. 1 is a bar graph showing percent changes in trabecular density, for: (a) Sham operation, no drug; (b) OVX operation, no drug; (c) OVX operation, ABD68 (20 mg/kg, orally); (d) OVX operation, ABD355 (20 mg/kg, orally); (e) OVX operation, ABD328 (20 mg/kg, orally). The graph shows that OVX causes a 34% decrease in trabecular bone density relative to the control group. The groups treated with ABD68 and ABD355 show 21% and 10% decreases respectively, whereas the group treated with ABD328 shows a 6% increase in trabecular bone density.

One aspect of the present invention pertains to compounds selected from compounds of the following formula and pharmaceutically acceptable salts, solvates, and hydrates thereof (hereinafter collectively referred to as "DCBP compounds"):

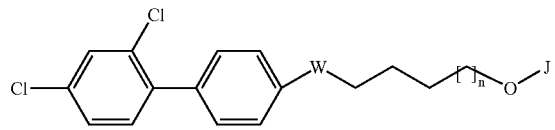

wherein:
n is independently 1, 2, 3, or 4;
W is independently —C(=O)—, —CH(OH)—, or —C(=NOR$^{OX}$)—;
R$^{OX}$ is independently —H or C$_{1-3}$alkyl;
J is independently:
—H,
—R$^{E1}$,
—C(=O)—R$^{E2}$,
—C(=O)—O—R$^{E3}$,
—C(=O)—O—S(=O)$_2$OR$^{E4}$,
—C(=O)—(CH$_2$)$_n$—C(=O)OR$^{E5}$,
—C(=O)—(CH$_2$)$_n$—NR$^{NE1}$R$^{NE2}$,
—C(=O)—(CH$_2$)$_n$—NR$^{NE3}$—C(=O)R$^{E6}$,
—C(=O)—(CH$_2$)$_n$—C(=O)—NR$^{NE4}$R$^{NE5}$, or
—P(=O)(OR$^{E7}$)(OR$^{E8}$);

wherein each of R$^{E1}$, R$^{E2}$, R$^{E3}$, R$^{E4}$, R$^{E5}$, R$^{E6}$, and R$^{E7}$ is independently:
—H, C$_{1-3}$alkyl, -Ph, or —CH$_2$-Ph.
In one embodiment, n is independently 1, 2, 3, or 4.
In one embodiment, n is independently 2, 3, or 4.
In one embodiment, n is independently 2 or 3.
In one embodiment, n is independently 2.
In one embodiment, n is independently 3.
In one embodiment, W is independently —C(=O)—, —CH(OH)—, or —C(=NOR$^{OX}$)—;
In one embodiment, W is independently —C(=O)— or —C(=NOR$^{OX}$)—.
In one embodiment, W is independently —C(=O)— or —CH(OH)—.
In one embodiment, W is independently —C(=O)—.
In one embodiment, W is independently —CH(OH)—.
In one embodiment, W is independently —C(=NOR$^{OX}$)—.
In one embodiment, R$^{OX}$, if present, is independently —H or C$_{1-3}$alkyl;
In one embodiment, R$^{OX}$, if present, is independently —H, -Me, or -Et.
In one embodiment, R$^{OX}$, if present, is independently —H.
In one embodiment, J is independently —H, R$^{E1}$, or —C(=O)—R$^{E2}$.
In one embodiment, J is independently —H.
In one embodiment, each of R$^{E1}$, R$^{E2}$, R$^{E3}$, R$^{E4}$, R$^{E5}$, R$^{E6}$ and R$^{E7}$, if present, is independently: —H, C$_{1-3}$alkyl, -Ph, or —CH$_2$-Ph.

In one embodiment, each of $R^{E1}$, $R^{E2}$, $R^{E3}$, $R^{E4}$, $R^{E5}$, $R^{E6}$, and $R^{E7}$, if present, is independently —H or $C_{1-3}$alkyl.

In one embodiment, each of $R^{E1}$, $R^{E2}$, $R^{E3}$, $R^{E4}$, $R^{E5}$, $R^{E6}$, and $R^{E7}$, if present, is independently —H, -Me, or -Et.

All plausible and compatible combinations of the embodiments described above are explicitly disclosed herein, as if each plausible and compatible combination was individually and explicitly recited.

It is noted that when W is —CH(OH)—, this carbon atom (indicated with an asterisk in the following formula) is a chiral centre, and the compound is optically active:

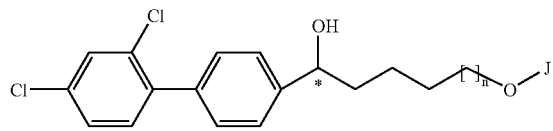

Some of the chemical structures shown herein indicate a specific stereoisomeric configuration. Some of the chemical structures shown herein are silent in this respect, and do not indicate a stereoisomeric configuration. Where a chemical structure herein is silent with respect to the stereoisomeric configuration at a position, that structure is intended to depict all possible stereoisomeric configuration at that position, both individually, as if each possible stereoisomeric configuration was individually recited, and also as a mixture (e.g., a racemic mixture) of stereoisomers.

In one embodiment, the compound is selected from compounds of the following formulae and pharmaceutically acceptable salts, solvates, and hydrates thereof:

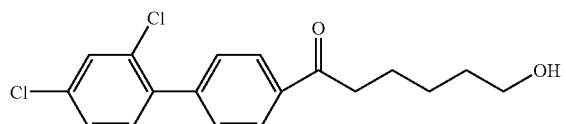

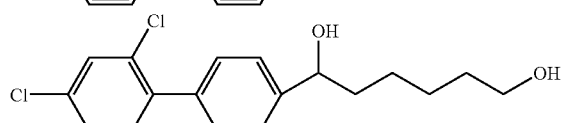

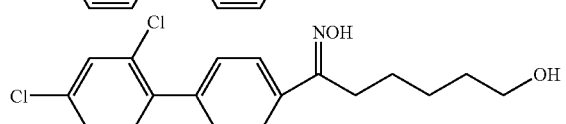

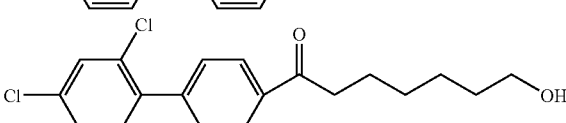

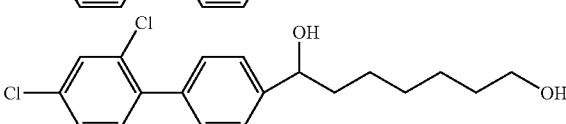

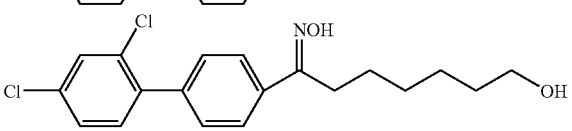

In one embodiment, the compound is selected from compounds of the following formulae and pharmaceutically acceptable salts, solvates, and hydrates thereof:

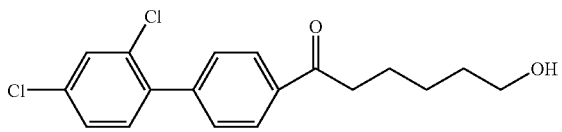

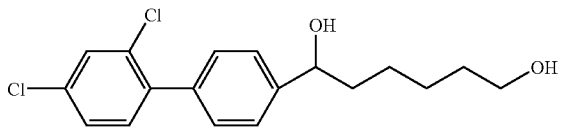

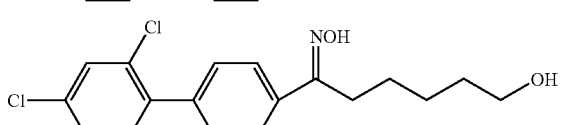

In one embodiment, the compound is selected from compounds of the following formulae and pharmaceutically acceptable salts, solvates, and hydrates thereof:

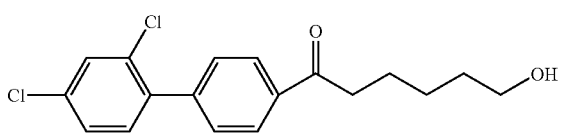

In one embodiment, the compound is selected from compounds of the following formulae and pharmaceutically acceptable salts, solvates, and hydrates thereof:

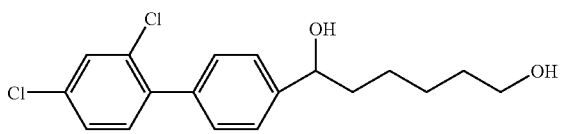

In one embodiment, the compound is selected from compounds of the following formulae and pharmaceutically acceptable salts, solvates, and hydrates thereof:

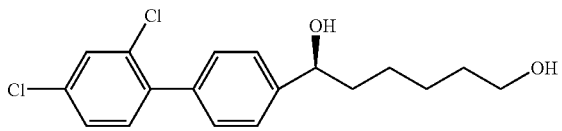

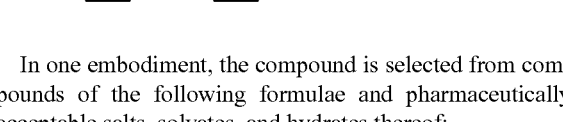

In one embodiment, the compound is selected from compounds of the following formulae and pharmaceutically acceptable salts, solvates, and hydrates thereof:

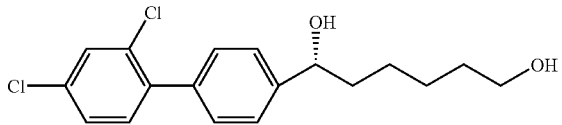

In one embodiment, the compound is:

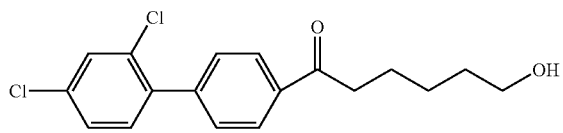

In one embodiment, the compound is:

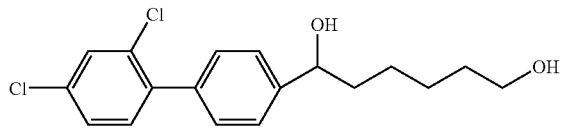

In one embodiment, the compound is:

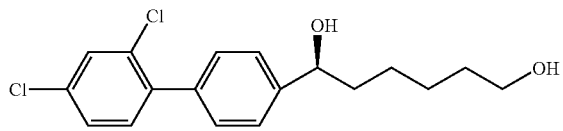

In one embodiment, the compound is:

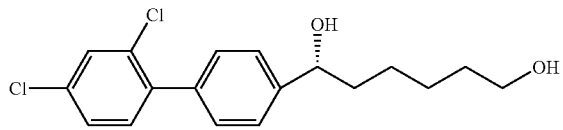

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemical Synthesis

The DCBP compounds described herein may be prepared, for example, by methods in which, first, para-bromobenzoic acid (1) is reacted with methanol to give the corresponding methyl ester (2). This ester is then reacted with 2,4-dichlorophenyl boronic acid to give the corresponding 2',4'-dichlorobiphenyl-4-carboxylic acid methyl ester (3). The ester group is then removed to give the corresponding acid (4), and the acid (4) is then converted to the corresponding acid chloride (5) using, for example, thionyl chloride. The acid chloride (5) is then converted to the corresponding methoxy methyl amide (6) using, for example, N,O-dimethyl hydroxylamine. The amide (6) is then reacted with a bromoalkene Grignard reagent to give the corresponding biphenyl alkene (7), which is then hydroxylated to give the corresponding biphenyl ketone alcohol (8).

An example of such a method is illustrated in the following scheme:

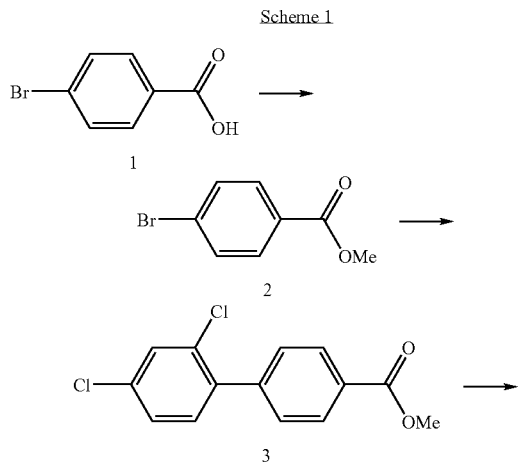

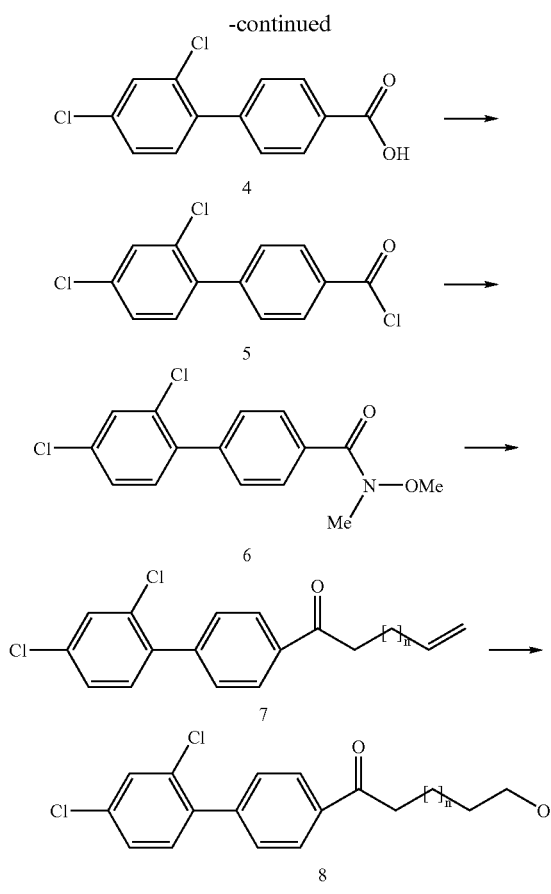

Corresponding oximes (where W is —C(=NOR$^{OX}$)—) (and which are, in effect, protected ketones) may be prepared, for example, by reacting the ketone (8) with hydroxylamine hydrochloride.

An example of such a method is illustrated in the following scheme:

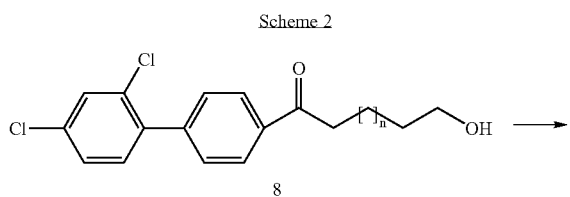

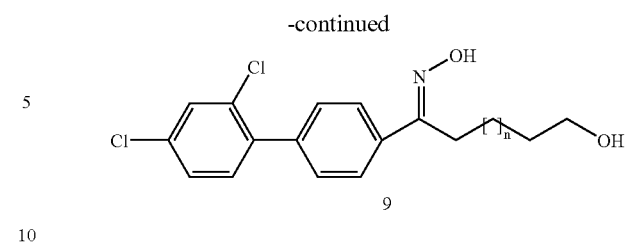

Corresponding hydroxyl compounds (where W is —CH(OH)—) (and which are, in effect, reduced ketones) may be prepared by reducing the parent ketone, for example, by using any of a number of selective and unselective reagents in order to yield either of the two possible enantiomers or a racemic mixture thereof. Examples of selective reagents include DIP-Cl (see, e.g., Ramachandran et al, 1995) and a range of chiral oxazaborolidines (see, e.g., Corey et al. 1988).

For example, in one method, the ketone (8) is reacted with a chiral oxazaborolidine to give, selectively, one of the two reduced ketone enantiomers (10).

An example of such a method is illustrated in the following scheme:

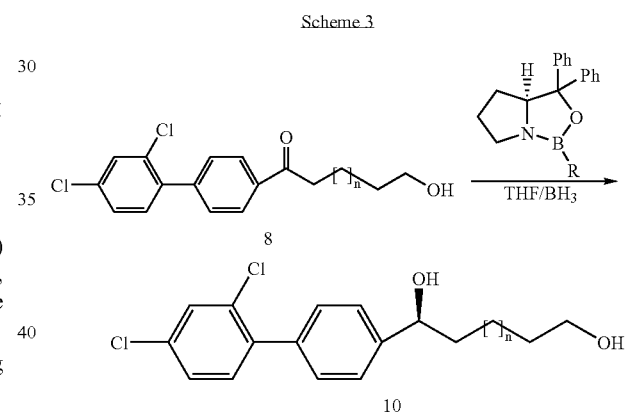

In another method, the alkene (7) is reacted with (+) or (−) DIP-chloride to give, selectively, one or the other of the two reduced ketone enantiomers (11) and (12), which can then be hydroxylated to give the corresponding biphenyl reduced ketone alkanols (13) and (14).

An example of such a method is illustrated in the following scheme:

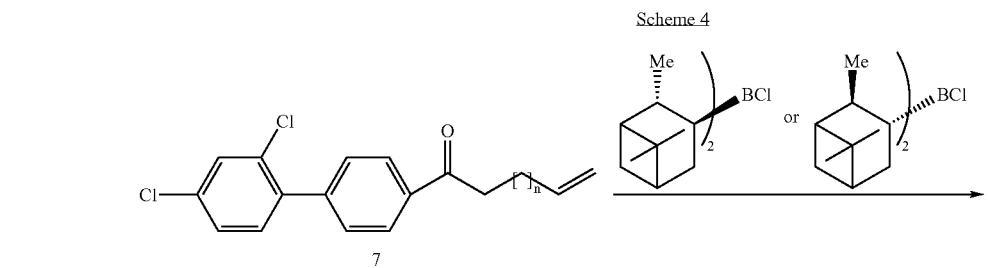

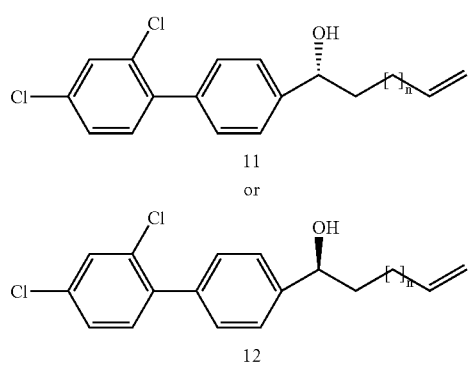

11
or

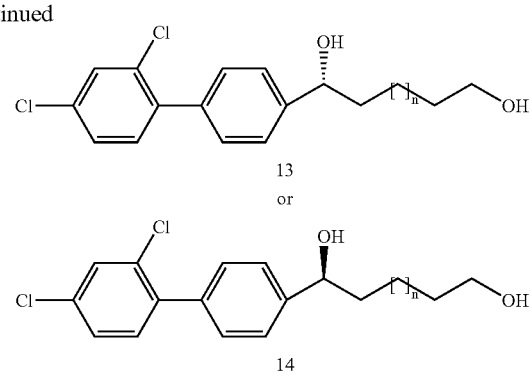

13
or

12

14

Acyl and phosphoryl esters may be prepared, for example, by reaction of the alcohol with the respective chloride or anhydride in the presence of a suitable base, such as pyridine.

Examples of such methods are illustrated in the following schemes:

Scheme 5

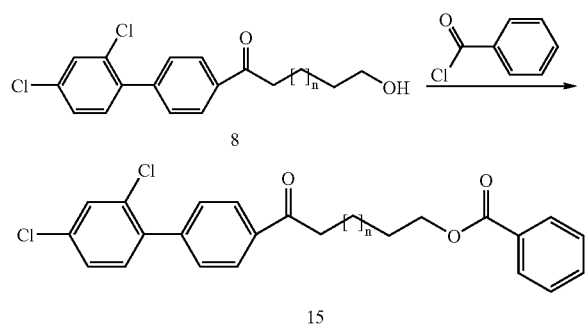

Scheme 6

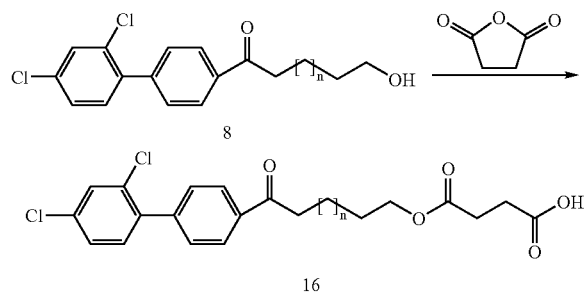

Scheme 7

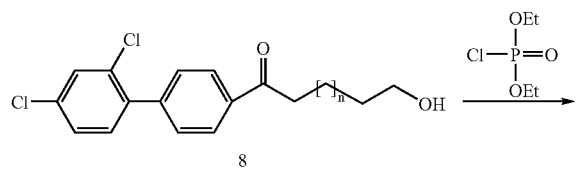

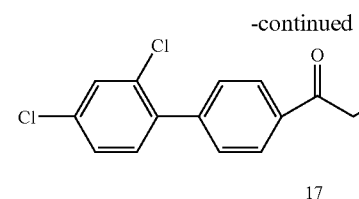

17

These methods and/or other well known methods may be modified and/or adapted in known ways in order to facilitate the synthesis of additional examples of the DCBP compounds described herein.

The products may be purified, for example, by column chromatography, trituration (e.g., with ether), or by crystallisation.

Examples of some suitable methods for the synthesis of the compounds of the present invention are described in the Examples below.

Uses

The DCBP compounds described herein are believed to be anti-inflammatory agents which may act by blockade or modification of pro-inflammatory signalling pathways (for example those mediated by TNFα signalling and NFκB or AP-1 activation) and thus may prevent inflammation or suppress autoimmune responses or offer protection against joint destruction and other effects of chronic inflammatory disease.

The DCBP compounds described herein are also believed to be anti-resorptive agents which may act by blockade or modification of pathways which lead to excessive osteoclast activity (for example those mediated by RANKL, TNFα, and IL-1 signalling and NFκB activation) and thereby protect against the bone loss seen in osteoporosis and many chronic inflammatory conditions.

Thus, the DCBP compounds described herein are believed to be useful in the treatment and/or prevention of inflammation and/or joint destruction and/or bone loss.

Thus, the DCBP compounds described herein are believed to be useful in the treatment and/or prevention of disorders mediated by excessive and/or inappropriate and/or prolonged activation of the immune system.

Thus, the DCBP compounds described herein are believed to be useful in the treatment and/or prevention of, inflammatory and autoimmune disorders, for example, rheumatoid arthritis, psoriasis, psoriatic arthritis, inflammatory bowel disease, ankylosing spondylitis, and the like.

Thus, the DCBP compounds described herein are believed to be useful in the treatment and/or prevention of disorders associated with bone loss, such as bone loss associated with excessive osteoclast activation in rheumatoid arthritis, osteoporosis, cancer associated bone disease, Paget's disease and the like.

Use in Methods of Inhibition

One aspect of the invention pertains to a method of inhibiting an inflammatory response, in vitro or in vivo, comprising contacting an immune system component with an effective amount of a DCBP compound, as described herein.

One aspect of the invention pertains to a method of inhibiting cellular and/or molecular pathways leading to joint destruction, in vitro or in vivo, comprising contacting cells associated with an immune response with a therapeutically-effective amount of a DCBP compound, as described herein.

One aspect of the invention pertains to a method of inhibiting osteoclast survival, formation, and/or activity, in vitro or in vivo, comprising contacting an osteoclast with an effective amount of a DCBP compound, as described herein.

One aspect of the invention pertains to a method of inhibiting bone resorption, in vitro or in vivo, comprising contacting cells in the bone microenvironment with a therapeutically-effective amount of a DCBP compound, as described herein.

The term "immune system component," as used herein, relates to, but is not restricted to, cells such as macrophages, T-cells, B-cells, NK-cells, monocytes, neutrophils, dendritic cells, lymphocytes, leukocytes, granulocytes, antigen-presenting cells, and other cells of the haematopoietic lineage including osteoclasts.

The term "cells in the bone microenvironment," as used herein, pertains to cells such as osteoblasts, osteoclasts, osteocytes, and bone marrow stromal cells, which are located in close proximity to bone (e.g., within one hundred micrometers of the bone surface).

Use in Methods of Therapy

One aspect of the present invention pertains to a DCBP compound as described herein for use in a method of treatment and/or prevention of the human or animal body by therapy.

Use in the Manufacture of Medicaments

One aspect of the present invention pertains to use of a DCBP compound, as described herein, in the manufacture of a medicament for use in treatment and/or prevention.

Methods of Treatment

One aspect of the present invention pertains to a method of treatment and/or prevention comprising administering to a patient in need of treatment and/or prevention a therapeutically effective amount of a DCBP compound as described herein, preferably in the form of a pharmaceutical composition.

Diseases and Disorders

In one embodiment, the treatment and/or prevention is treatment and/or prevention of an inflammatory disorder or an autoimmune disorder.

In one embodiment, the treatment and/or prevention is treatment and/or prevention of a disorder associated with inflammation and/or activation of the immune system.

In one embodiment, the treatment and/or prevention is treatment and/or prevention of a disorder mediated by excessive and/or inappropriate and/or prolonged activation of the immune system.

In one embodiment, the treatment and/or prevention is treatment and/or prevention of inflammation.

In one embodiment, the treatment and/or prevention is treatment and/or prevention of a disorder associated with inflammation or activation of the immune system.

In one embodiment, the treatment and/or prevention is treatment and/or prevention of rheumatoid arthritis.

In one embodiment, the treatment and/or prevention is treatment and/or prevention of psoriasis.

In one embodiment, the treatment and/or prevention is treatment and/or prevention of psoriatic arthritis.

In one embodiment, the treatment and/or prevention is treatment and/or prevention of ankylosing spondylitis.

In one embodiment, the treatment and/or prevention is treatment and/or prevention of inflammatory bowel disease.

In one embodiment, the treatment and/or prevention is prevention of an immune response leading to organ or graft rejection following transplant.

In one embodiment, the treatment and/or prevention is treatment of a tumor which over expresses TNFα, IL-1, or RANKL or in which inhibition of TNFα, IL-1, or RANKL facilitates or improves the action of cytotoxic tumoricidal agents.

In one embodiment, the treatment and/or prevention is treatment and/or prevention of a disease or disorder selected from: diseases having an inflammatory or autoimmune component, including asthma, allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes, multiple sclerosis, arthritis, systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumors, types of type 1 hypersensitivity reactions (anaphylaxis, skin allergy, hives, gout, allergic rhinitis, and allergic gastroenteritis); ulcerative colitis or Crohn's disease.

In one embodiment, the treatment and/or prevention is treatment and/or prevention of a disorder mediated by osteoclasts.

In one embodiment, the treatment and/or prevention is treatment and/or prevention of a disorder characterised by excessive bone resorption.

In one embodiment, the treatment and/or prevention is treatment and/or prevention of bone loss.

In one embodiment, the treatment and/or prevention is treatment and/or prevention of bone loss associated with inflammation.

In one embodiment, the treatment and/or prevention is treatment and/or prevention of bone loss not associated with inflammation.

In one embodiment, the treatment and/or prevention is treatment and/or prevention of bone loss associated with excessive osteoclast activation.

In one embodiment, the treatment and/or prevention is treatment and/or prevention of joint destruction.

In one embodiment, the treatment and/or prevention is treatment and/or prevention of joint destruction associated with inflammation.

In one embodiment, the treatment and/or prevention is treatment and/or prevention of joint destruction associated with excessive osteoclast activation.

In one embodiment, the treatment and/or prevention is treatment and/or prevention of bone loss associated with rheumatoid arthritis, osteoporosis, cancer associated bone disease, or Paget's disease of bone.

In one embodiment, the treatment and/or prevention is treatment and/or prevention of rheumatoid arthritis, osteoporosis, cancer associated bone disease, or Paget's disease of bone.

In one embodiment, the treatment and/or prevention is treatment and/or prevention of neoplasia of bones, whether as a primary tumour and as metastases, including but not limited to, osteosarcoma and osteoma (Zheng et al., 1998, *J. Cell Biochem.*, Vol. 70, p. 121) and cancer associated bone disease (e.g., hypercalcaemia of malignancy, bone metastases, osteolytic bone metastases, multiple myeloma, breast carcinoma).

In one embodiment, the treatment and/or prevention is treatment and/or prevention of hypercalcaemia caused by conditions associated with increased bone resorption, including, but not limited to: vitamin D intoxication, primary or tertiary hyperparathyroidism, immobilisation, and sarcoidosis.

In one embodiment, the treatment and/or prevention is treatment and/or prevention of aseptic loosening of prosthetic implants (e.g., artificial joints, e.g., knees, hips, etc., can loosen due to osteoclast activity driven by local inflammation) (see, e.g., Childs, L. M., et al., 2001, *Journal of Bone and Mineral Research*, Vol. 16, No. 2, pp. 338-347).

In one embodiment, the treatment and/or prevention is treatment and/or prevention of osteopetrosis, osteoarthritis, or ectopic bone formation.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included. For example, use with perimenopausal women who may not yet have osteoporosis, but who are at risk of osteoporosis, is encompassed by the term "treatment."

The term "therapeutically-effective amount," as used herein, pertains to that amount of a DCBP compound, or a material, composition or dosage from comprising a DCBP compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Other Uses

DCBP compounds, as described herein, may also be used as cell culture additives to inhibit immune cell function, for example, to inhibit the survival, formation, and/or activity of macrophages, T-cells, or other cells involved in the immune response.

The DCBP compounds, as described herein, may also be used as cell culture additives, for example, to inhibit osteoclasts, for example, to inhibit the survival, formation, and/or activity of osteoclasts.

The DCBP compounds, as described herein, may also be used as part of an in vitro assay, for example, in order to determine whether a candidate host is likely to benefit from treatment with the compound in question.

The DCBP compounds, as described herein, may also be used as a standard, for example, in an assay, in order to identify other active compounds, other osteoclast inhibitors, etc.

Kits

One aspect of the invention pertains to a kit comprising (a) a DCBP compound as described herein, or a composition comprising a DCBP compound as described herein, e.g., preferably provided in a suitable container and/or with suitable packaging; and (b) instructions for use, e.g., written instructions on how to administer the DCBP compound or composition.

The written instructions may also include a list of indications for which the DCBP compound is a suitable treatment.

Routes of Administration

The DCBP compound or pharmaceutical composition comprising the DCBP compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

An especially preferred route of administration is oral (e.g., by ingestion).

The Subject/Patient

The subject/patient may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject/patient may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the DCBP compound to be administered alone, it is preferable to present it as a pharmaceutical formulation (e.g., composition, preparation, medicament) comprising at least one DCBP compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one DCBP compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the DCBP compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 2nd edition, 1994.

The formulations may be prepared by any methods well known in the art of pharmacy. Such methods include the step of bringing into association the DCBP compound with a carrier which constitutes one or more accessory ingredients. In general, the formulations are prepared by uniformly and intimately bringing into association the DCBP compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more DCBP compounds and optionally one or more other pharmaceutically acceptable ingredients, including, for example, penetration, permeation, and absorption enhancers. Formulations may also suitably be provided in the form of a depot or reservoir.

The DCBP compound may be dissolved in, suspended in, or admixed with one or more other pharmaceutically acceptable ingredients. The DCBP compound may be presented in a liposome or other microparticulate which is designed to target the DCBP compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the DCBP compound in a flavored basis, usually sucrose and acacia or tragacanth. Pastilles typically comprise the DCBP compound in an inert matrix, such as gelatin and glycerin, or sucrose and acacia. Mouthwashes typically comprise the DCBP compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the DCBP compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the DCBP compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the DCBP compound and a paraffinic or a water-miscible ointment base.

Creams are typically prepared from the DCBP compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the DCBP compound through the skin or other affected areas. Examples of such dermal penetration enhancers include dimethylsulfoxide and related analogues.

Emulsions are typically prepared from the DCBP compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the DCBP compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the DCBP compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for ocular administration include eye drops wherein the DCBP compound is dissolved or suspended in a suitable carrier, especially an aqueous solvent for the DCBP compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the DCBP compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the DCBP compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the DCBP compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the DCBP compounds, and compositions comprising the DCBP compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the DCBP compound is in the range of about 100 µg to about 250 mg (more typically about 100 µg to about 25 mg) per kilogram body weight of the subject per day. Where the DCBP compound is a salt, a hydrate, or a solvate, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Synthesis 1

4-Bromo-benzoic acid methyl ester

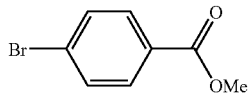

4-Bromo-benzoic acid (5 g) was suspended in methanol (50 mL) and conc. $H_2SO_4$ (5 mL) added. The mixture was heated to reflux for 3 hours. Evaporation of some of the methanol led to crystallisation. The solid was collected and dissolved in DCM, washed with $NaHCO_3$, and dried. Methanol (10 mL) was added and the solvents were evaporated until crystallisation occurred. The solid was collected and recrystallised from methanol to give the title compound as white needles. $^{13}C$ NMR ($CDCl_3$): δ 52.3, 128.1, 129.0, 131.1, 131.7 and 166.3. $^1H$ NMR ($CDCl_3$): δ 3.88 (3H, s), 7.55 (2H, d, J=8.2 Hz) and 7.87 (2H, d, J=8.2 Hz).

Synthesis 2

2',4'-Dichloro-biphenyl-4-carboxylic acid methyl ester

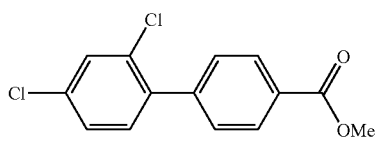

4-Bromo-benzoic acid methyl ester (3 g) was dissolved in a mixture of toluene (20 mL) and ethanol (20 mL). 2,4-Dichloro-phenyl boronic acid (3 g) was added followed by 2 M $Na_2CO_3$ (20 mL). The mixture was stirred vigorously under $N_2$ and $(PPh_3)_4Pd$ (0.5 g) added. The mixture was refluxed with stirring for 3 hours under an atmosphere of $N_2$. The solvent was removed under vacuum, the residue was dissolved in ethyl acetate, and washed with water and saturated NaCl solution. After drying ($Na_2SO_4$), the solvent was evaporated and the resultant oil purified by column chromatography to give a fluffy white powder, which was recrystallised from ethanol to give the title compound as long needles. $^{13}C$ NMR ($CDCl_3$): δ 52.3, 127.3, 129.5, 129.5, 129.6, 129.9, 131.9, 133.1, 134.4, 138.1, 142.8 and 166.8. $^1H$ NMR ($CDCl_3$): δ 3.93 (3H, s), 7.27 (2H, m), 7.47 (2H, d, J=8.5 Hz), 7.49 (1H, s) and 8.09 (2H, d, J=8.2 Hz).

Synthesis 3

2',4'-Dichloro-biphenyl-4-carboxylic acid

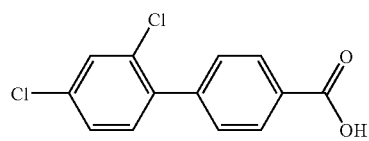

2',4'-Dichloro-biphenyl-4-carboxylic acid methyl ester (3 g) was dissolved in a mixture of THF (25 mL) and methanol (25 mL). 1 M NaOH (50 mL) was added and the mixture stirred for 4 hours by which stage a clear solution had formed. Conc. HCl was added and the precipitate was collected as a white solid. Toluene was added and the mixture was evaporated to dryness to give the title compound as a white solid. $^1H$ NMR ($CDCl_3$): δ 7.20 (2H, m), 7.52 (2H, m), 7.64 (1H, s) and 8.12 (2H, m).

Synthesis 4

2',4'-Dichloro-biphenyl-4-carbonyl chloride

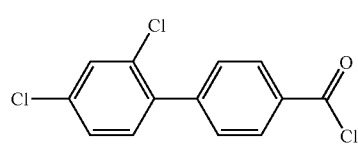

2',4'-Dichloro-biphenyl-4-carboxylic acid (2 g) was suspended in toluene (30 mL) and thionyl chloride (5 mL) added. The mixture was heated to reflux for 4 hours and then evaporated to dryness and the procedure repeated. Evaporation gave the title compound as a white solid.

Synthesis 5

2',4'-Dichloro-biphenyl-4-carboxylic acid methoxy-methyl-amide

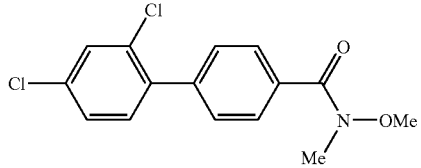

2',4'-Dichloro-biphenyl-4-carbonyl chloride was dissolved in chloroform (10 mL) and added dropwise to a chilled solution of N,O-dimethyl hydroxylamine (2.5 g) and triethylamine (7 mL) in chloroform (40 mL). Following addition, the mixture was allowed to warm to room temperature and stirred for a further 30 minutes. The mixture was poured into water and the organic phase separated, washed with water, and dried. Evaporation gave an oil, which was purified by column chromatography (petrol/ethyl acetate) to give a pale yellow oil which slowly crystallised upon standing to give the title compound as a white solid. $^{13}$C NMR (CDCl$_3$): δ 33.8, 61.2, 127.3, 128.2, 129.1, 129.9, 132.0, 133.2, 133.5, 134.2, 138.3, 140.5 and 169.5. $^1$H NMR (CDCl$_3$): δ 3.39 (3H, s), 3.58 (3H, s), 7.26 (2H, m), 7.45 (2H, d, J=8.5 Hz), 7.54 (1H, s) and 8.08 (2H, d, J=8.5 Hz).

Synthesis 6

1-(2',4'-Dichloro-biphenyl-4-yl)-hex-5-en-1-one

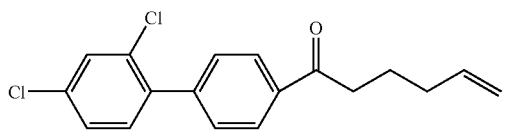

5-Bromo-1-pentene (5 g) was gently heated with magnesium turnings (1 g) in anhydrous tetrahydrofuran (25 mL) until reaction started. The mixture was left to reflux without further heating to give the Grignard reagent, then allowed to cool to room temperature. 2',4'-Dichloro-biphenyl-4-carboxylic acid methoxy-methyl-amide (2 g) was dissolved in anhydrous tetrahydrofuran (25 mL) and chilled in an ice bath. The above Grignard reagent was added dropwise with vigorous stirring. Following addition, the mixture was allowed to warm to room temperature and stirring continued for 2 hours. Saturated NH$_4$Cl solution (50 mL) was added and the mixture extracted with petrol. Drying with Na$_2$SO$_4$ and evaporation gave an oil. Column chromatography (petrol:ethyl acetate) gave the title compound as a clear oil which solidified overnight. $^{13}$C NMR (CDCl$_3$): δ 23.4, 33.3, 37.8, 115.3, 127.4, 128.0, 129.7, 129.9, 131.9, 133.1, 134.5, 136.3, 138.0, 138.4, 142.8 and 199.9. $^1$H NMR (CDCl$_3$): δ 1.85 (2H, t, J=7.0 Hz), 2.18 (2H, t, J=7.0 Hz), 3.03 (2H, t, J=7.3 Hz), 5.01 (2H, m), 5.87 (1H, m), 7.28 (2H, d, J=8.2 Hz), 7.31 (1H, s), 7.52 (2H, m) and 8.00 (2H, m).

Synthesis 7

1-(2',4'-Dichloro-biphenyl-4-yl)-6-hydroxy-hexan-1-one (ABD328)

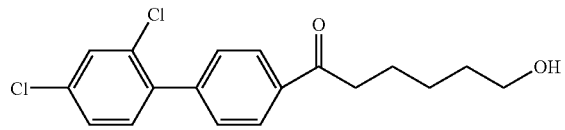

1-(2',4'-Dichloro-biphenyl-4-yl)-hex-5-en-1-one (1.1 g) was dissolved in 0.5 M 9-BBN (6.9 mL) and stirred at room temperature for 4 hours. Sodium perborate (1 g) was added and the mixture stirred at room temperature for 1 hour. Water (3 mL) was added and the mixture stirred at 50° C. for 2 hours, then overnight at room temperature. The mixture was extracted with ether, dried, and evaporated to give an oil. The oil was purified by column chromatography to give an oil which solidified to a white amorphous solid on standing, and which was recrystallised from ether/petrol to give the title compound as a white powder. $^{13}$C NMR (CDCl$_3$): δ23.9, 25.5, 32.5, 38.6, 62.7, 127.4, 128.0, 129.7, 129.9, 131.9, 133.1, 134.5, 136.3, 138.0, 142.8 and 199.9. $^1$H NMR (CDCl$_3$): δ 1.45 (2H, m), 1.60 (2H, m), 1.80 (2H, m), 3.01 (2H, t, J=6.5 Hz), 3.68 (2H, t, J=6.5 Hz), 7.28 (2H, d, J=8.2 Hz), 7.30 (1H, s), 7.50 (2H, m) and 8.01 (2H, d, J=8.2 Hz).

Synthesis 8

1-(2',4'-Dichloro-biphenyl-4-yl)-6-hydroxy-hexan-1-one oxime (ABD468)

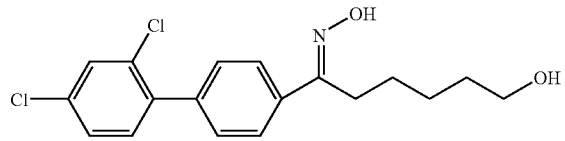

1-(2',4'-Dichloro-biphenyl-4-yl)-6-hydroxy-hexan-1-one (400 mg) was dissolved in a mixture of ethanol (10 mL) and water (5 mL). Hydroxylamine hydrochloride (300 mg) and sodium acetate (350 mg) were added and the mixture refluxed for 5 hours. After cooling, the mixture was diluted with water and extracted with ethyl acetate. Evaporation and recrystallisation from ether/petrol gave the title compound as a white solid. $^{13}$C NMR (CDCl$_3$): δ 25.9, 26.2, 26.2, 32.3, 62.8, 126.1, 127.3, 129.6, 129.8, 132.0, 133.2, 134.0, 135.2, 138.4, 139.1 and 159.3. $^1$H NMR (CDCl$_3$): δ 1.45 (2H, m), 1.59 (4H, m), 2.80 (2H, m), 3.62 (2H, m), 7.26 (2H, m), 7.41 (2H, d, J=7.0 Hz), 7.47 (1H, m) and 7.64 (2H, d, J=7.0 Hz).

Synthesis 9

1-(4-Bromo-phenyl)-hex-5-en-1-ol

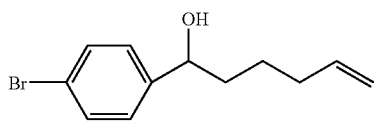

4-bromo-benzyl-carboxaldehyde (3 g) was dissolved in anhydrous diethyl ether (30 mL) and was reacted with a Grignard reagent prepared from 5-bromo-pentene and magnesium as described in Synthesis 6 above. The mixture was stirred for 30 minutes and a saturated solution of $NH_4Cl$ was added. The mixture was extracted with petrol, dried and evaporated to give an oil. The oil was purified by column chromatography to give a mixture of the title compound and 5-bromo-pentene. $^{13}C$ NMR ($CDCl_3$): δ 24.9, 33.5, 38.5, 73.9, 114.9, 121.2, 127.6, 131.5, 138.4 and 143.8. $^1H$ NMR ($CDCl_3$): δ 1.34 (2H, m), 1.75 (2H, m), 1.90 (2H, m), 4.61 (1H, t, J=6.1 Hz), 4.94 (2H, m), 5.75 (1H, m), 7.19 (2H, d, J=8.2 Hz) and 7.45 (2H, d, J=8.2 Hz).

Synthesis 10

1-(4-Bromo-phenyl)-hexane-1,6-diol

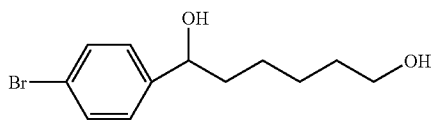

1-(4-Bromo-phenyl)-hex-5-en-1-ol (1 g) was dissolved in 0.5 M $NaBH_4$ in diglyme (9 mL) and chilled in an ice bath. $BF_3.OEt_2$ (1 mL) in diglyme (4 mL) was added with vigorous stirring. Stirring was continued for 1 hour and water (1 mL) was added. 3M NaOH (2 mL) was added followed by 30% $H_2O_2$ (3 mL). Anhydrous $K_2CO_3$ (5 g) was added and the solvent was decanted. The $K_2CO_3$ was washed with ethyl acetate and the combined organics were dried ($Na_2SO_4$) and evaporated. Distillation under vacuum removed most of the remaining diglyme. The residue was purified by column chromatography (light petroleum:diethyl ether 2:1) to give a clear oil which solidified to give the title compound as a white powder. $^{13}C$ NMR ($CDCl_3$): δ 25.4, 25.6, 32.5, 39.0, 62.7, 73.8, 121.2, 127.7, 131.5 and 143.9. $^1H$ NMR ($CDCl_3$): δ 1.40 (4H, m), 1.52 (2H, m), 1.74 (2H, m), 3.61 (2H, t, J=6.5 Hz), 4.74 (1H, t, J=6.5 Hz), 7.20 (2H, d, J=8.2 Hz) and 7.41 (2H, d, J=8.2 Hz).

Synthesis 11

(R,S)-1-(2',4'-Dichloro-biphenyl-4-yl)-hexane-1,6-diol (ABD300)

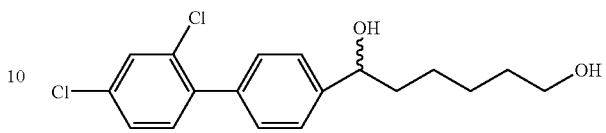

1-(4-Bromo-phenyl)-hexane-1,6-diol (0.5 g) was dissolved in a mixture of toluene (8 mL) and ethanol (8 mL). 2,4-Dichlorophenyl boronic acid (0.7 g) was added followed by 2 M $Na_2CO_3$ (8 mL). The mixture was stirred vigorously under $N_2$ and $(PPh_3)_4Pd$ (0.25 g) added. The mixture was refluxed with stirring for 3 hours under an atmosphere of $N_2$. The solvent was removed under vacuum, the residue dissolved in ethyl acetate and washed with water and saturated NaCl solution. After drying ($Na_2SO_4$), the solvent was evaporated and the resultant oil was purified by column chromatography to give a yellow oil which slowly solidified to give the title compound as an amorphous yellow powder. $^{13}C$ NMR ($CDCl_3$): δ 25.6, 25.6, 32.6, 39.0, 62.8, 74.2, 125.7, 127.2, 129.5, 129.8, 132.1, 133.2, 133.7, 137.5, 138.7 and 144.6. $^1H$ NMR ($CDCl_3$): δ 1.38 (4H, m), 1.54 (2H, m), 1.79 (2H, m), 3.63 (2H, t, J=6.4 Hz), 4.72 (1H, t, J=6.5 Hz), 7.26 (2H, m), 7.39 (4H, m) and 7.47 (1H, s).

Synthesis 12

(R)-1-(2',4'-Dichloro-biphenyl-4-yl)-hex-5-en-1-ol

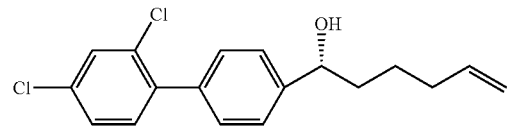

(+)DIP-Chloride (2.4 g) was dissolved in dry ether (10 mL) and cooled in an ethanol/$CO_2$ bath. 1-(2',4'-Dichloro-biphenyl-4-yl)-hex-5-en-1-one (1 g) was dissolved in dry ether (5 mL) and added dropwise to the DIP solution. The mixture was allowed to warm to room temperature and stirred for 24 hours. Petrol (50 mL) was added and the organic layer was separated. The aqueous layer was diluted with water and extracted with a further 50 mL petrol. The organics were combined, dried and evaporated to give a thick oil. It was not possible to obtain a pure sample by column chromatography, but no trace of starting material remained, as assessed by thin layer chromatography.

Synthesis 13

(R)-1-(2',4'-Dichloro-biphenyl-4-yl)-hexane-1,6-diol (ABD511)

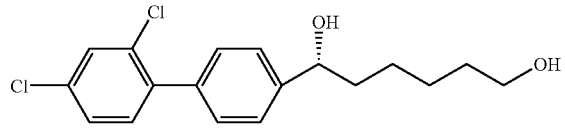

Impure (R)-1-(2',4'-dichloro-biphenyl-4-yl)-hex-5-en-1-ol (1 g) was dissolved in 0.5 M $NaBH_4$ in diglyme (9 mL) and chilled in an ice bath. $BF_3 \cdot OEt_2$ (1 mL) in diglyme (4 mL) was added with vigorous stirring. Stirring was continued for 1 hour and water (1 mL) was added. 3 M NaOH (2 mL) was added followed by 30% $H_2O_2$ (3 mL). Anhydrous $K_2CO_3$ (5 g) was added and the solvent was decanted. The $K_2CO_3$ was washed with ethyl acetate and the combined organics were dried ($Na_2SO_4$) and evaporated. Distillation under vacuum removed most of the remaining diglyme. The residue was purified by column chromatography (light petroleum:diethyl ether 2:1) to give a clear oil which crystallised on standing to give the title compound as white needles. $^{13}C$ NMR ($CDCl_3$): δ 25.7, 25.7, 32.6, 39.1, 62.9, 74.3, 125.7, 127.2, 129.5, 129.7, 132.1, 133.2, 133.7, 137.5, 138.7 and 144.6.

Synthesis 14

(S)-1-(2',4'-Dichloro-biphenyl-4-yl)-hex-5-en-1-ol

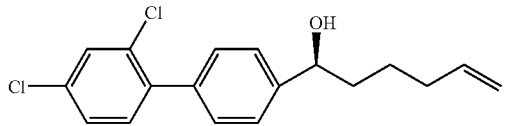

(−)DIP-Chloride (2.4 g) was dissolved in dry ether (10 mL) and cooled in an ethanol/$CO_2$ bath. 1-(2',4'-Dichloro-biphenyl-4-yl)hex-5-en-1-one (1 g) was dissolved in dry ether (5 mL) and added dropwise to the DIP solution. The mixture was allowed to warm to room temperature and stirred for 24 hours. Petrol (50 mL) was added and the organic layer separated. The aqueous was diluted with water and extracted with a further 50 mL petrol. The organics were combined, dried and evaporated to give a thick oil. It was not possible to obtain a pure sample by column chromatography, but no trace of starting material remained, as assessed by thin layer chromatography.

Synthesis 15

(S)-1-(2',4'-Dichloro-biphenyl-4-yl)-hexane-1,6-diol (ABD513)

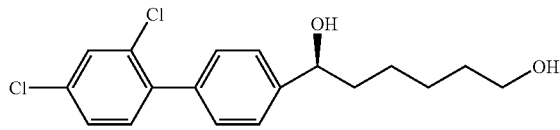

Impure (S)-1-(2',4'-dichloro-biphenyl-4-yl)hex-5-en-1-ol (1 g) was dissolved in 0.5 M $NaBH_4$ in diglyme (9 mL) and chilled in an ice bath. $BF_3 \cdot OEt_2$ (1 mL) in diglyme (4 mL) was added with vigorous stirring. Stirring was continued for 1 hour and water (1 mL) was added. 3 M NaOH (2 mL) was added followed by 30% $H_2O_2$ (3 mL). Anhydrous $K_2CO_3$ (5 g) was added and the solvent was decanted. The $K_2CO_3$ was washed with ethyl acetate and the combined organics were dried ($Na_2SO_4$) and evaporated. Distillation under vacuum removed most of the remaining diglyme. The residue was purified by column chromatography (light petroleum:diethyl ether 2:1) to give the title compound as a clear oil. $^{13}C$ NMR ($CDCl_3$): δ 25.6, 25.6, 32.6, 39.0, 62.8, 74.2, 125.7, 127.2, 129.5, 129.7, 132.1, 133.2, 133.7, 137.5, 138.7 and 144.6.

Biological Methods

Initial screening of candidate compounds was performed using viability assays on cultures of the macrophage cell line J774, which have been used before as a model system for osteoclast survival (see, e.g., Luckman et al., 1998). The assays are based on the survival of the J774 macrophage cell line; macrophages are closely related to osteoclasts, and contain similar high levels of esterase activity.

Alamar Blue Macrophage J774 Viability Assay

J774 cells were plated at $10^4$ cells per well in 150 μL αMEM (α Modified Eagle Medium) in 96-well plates and grown overnight. The next day, test compounds were added to the cultures, and cultures were continued for another 72 hours. At the end of the culture period, cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance is measured at 570 nm (reduced form) and 600 nm (oxidised form) and a simple calculation performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to the each well (1:10 v/v, 15 μL). The plate was incubated at 37° C. for 3-4 hours and the fluorescence was measured at 590 nm, with a 25 nm bandwidth. A high reading indicated cells with normal viability, and a low reading indicated cells that have been damaged and are no longer proliferating normally. The controls gave a high fluorescence reading, indicating a high number of live, healthy cells. A potent test compound gave a low fluorescence reading. The average results for each test compound (n=5) were expressed as a percent (%) of the average control value.

Addition of Compounds. All of the compounds studied were made up as 100 mM solutions in DMSO. These stock solutions were then diluted 100 or 1000× in culture medium (αMEM). From these 1 mM or 100 μM solutions, convenient quantities (3-15 μL) were added directly to the wells so as to give the desired final compound concentration.

This assay offers numerous advantages over other assays, including MTT assays: it permits a higher throughput; it is more sensitive; it is non-damaging to the cells; it is faster; it generally gives an identical result to MTT assay.

In Vivo Studies

Animals. Female 9 week-old C57/BL6 mice were used. Animals were housed in a designated animal facility and routinely maintained on a 12 hour:12 hour light:dark cycle and given ad libitum access to food and water.

Ovariectomy induced bone loss. Bilateral ovariectomy (Ovx) was performed under general anaesthesia. Sham ovariectomy (Sham) was similarly performed but with externalisation and replacement of the ovaries. Animals were given a daily injection of (a) test compound (e.g., 10 mg/kg) in vehicle (corn oil), or (b) vehicle (corn oil). After 21 days, the animals were killed, and the tibial bones were dissected and used for bone mineral density measurements and histomorphometric analysis (see below).

Bone Mineral Measurements. Measurements of bone mineral density (BMD) at the left proximal tibial metaphysis were determined by peripheral quantitative computed tomography (pQCT) using an XCT Research M bone densitometer with a voxel size of 70 μm and analysis software version 5.1.4 (Stratec Medizintechnik, Pforzheim, Germany). Daily quality assurance measurements were performed using a plexicoated PVC-fluorinated hydrocarbon phantom according to the manufacturer's instructions.

Bone Histomorphometry. Histomorphometry was performed on left tibiae. The bones were dissected free of soft tissues, fixed in 4% buffered formalin/saline (pH 7.4) and embedded in methyl methacrylate. Longitudinal sections (4 μm) were then prepared and stained with Von Kossa and counterstained with Paragon. Histomorphometric measurements were made on sections of the proximal metaphysis distal to the epiphyseal growth plate at 20× magnification using a Zeiss Axioskop (Carl Zeiss, Welwyn Garden City, UK) coupled to an image analysis system running in-house designed software developed using Aphelion ActiveX Objects (Adcis S A, Hérouville-Saint-Clair, France). Bone histomorphometric variables were expressed according to the guidelines of the American Society of Bone and Mineral Research Nomenclature Committee (Eriksen, E. F., Axelrod, D. W., Melsen., F, 1994, *Bone Histomorphometry*, Raven Press, New York, USA).

Statistical Analyses. Statistical analyses were performed using SPSS for Windows® version 9. Significant differences between groups were determined by ANOVA followed by post-hoc testing using Dunnet's post-test. All data are presented as means ±SEM unless stated otherwise. Values of p less than 0.05 were considered significant.

Dual Energy X-Ray Absorptiometry

Whole body, spine, and femoral bone mineral density (BMD) and bone mineral content (BMC) were determined using a Piximus small animal DEXA scanner at the start and the end of the experiment. Daily quality assurance measurements were performed using a phantom according to the manufacturer's instructions.

Collagen-Induced Arthritis

Collagen-induced arthritis (CIA) was induced in 8-week old male DBA/1 mice, by intradermal injection of 100 μL of chicken collagen type II (2 mg/mL) suspended in complete Freund's adjuvant supplemented with 2 mg/mL devitalised *M. Tuberculosis* into the base of the tail. This will lead to joint inflammation in >80% of the animals within 4 weeks. Treatment with ABD328 (10 mg/kg/day, orally or i.p., delivered in corn oil) was started when joint inflammation became apparent in the first animals (in this experiment 15 days after injection), and the experiment was terminated 3 weeks later. The animals were scored for joint inflammation at least 3 times per week using the scoring system shown in the following table. For each animal, the scores for all four joints were added (maximal score=12).

TABLE 1

Scoring Criteria

| Score | Criteria |
|---|---|
| 0 | Normal |
| 1 | Mild inflammation, limited to individual digits, regardless of the number of affected digits |

TABLE 1-continued

Scoring Criteria

| Score | Criteria |
|---|---|
| 2 | Moderate redness and swelling of ankle or wrist |
| 3 | Severe redness and swelling of the entire paw including digits |

Pharmacokinetics Studies

Absorption and metabolic stability were studied using an in vivo pharmacokinetics assay. Drug levels assessed using HPLC/UV.

Following overnight starvation, male Wistar rats (250 g) were given a bolus gavage of 500 μL of a solution of test compound in corn oil (5 mg/ml). Blood samples (1 mL, whole blood) were taken at various time intervals and the serum collected following centrifugation. Samples were frozen until required for analysis.

Ethyl acetate (4 mL) was added to the defrosted serum and the samples mixed for 20 minutes. Following centrifugation, the ethyl acetate layer was collected and evaporated under a stream of nitrogen. The residue was reconstituted in mobile phase and 20 μL injected onto the chromatogram.

Standard calibration curves were prepared for each of the test compounds and were linear in the range of 1 ng/mL to 250 ng/mL.

Chromatographic Conditions:

Column: HIRPB C18 (150×4.6 mm).

Mobile phase: 60% 25 mM ammonium acetate, pH 4; 40% acetonitrile.

Flow rate: 1 mL/minute.

Detection: Peaks detected by UV absorption at $\lambda_{max}$ in the range of 240-275 nm.

BIOLOGICAL DATA

Biological Study 1

The biological activity of 1-(2',4'-dichloro-biphenyl-4-yl)-6-hydroxy-hexan-1-one (ABD328) can be compared to a range of related derivatives using the assays described previously. For example, $IC_{50}$ values were determined for several biphenyl compounds using the Alamar Blue macrophage J774 viability assay described above. The results are summarised in the following table. These results demonstrate that ABD328 is of comparable potency to other related derivatives.

TABLE 2

Alamar Blue Macrophage J774 Viability Assay

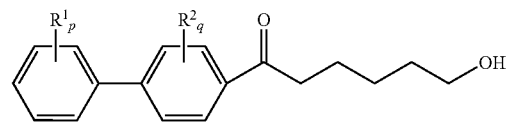

| Compound | $R^1_p$ | $R^2_q$ | $IC_{50}$ (μM) |
|---|---|---|---|
| ABD328 | 2,4-Dichloro | Unsubstituted | 12 ± 2 |
| ABD355 | 2,4-Difluoro | Unsubstituted | 7 ± 2 |
| ABD345 | 2,4-Difluoro | 2-Methyl | 8 ± 1 |
| ABD428 | 2,4-Difluoro | 3-Methyl | 4 ± 2 |

TABLE 2-continued

Alamar Blue Macrophage J774 Viability Assay

| Compound | $R^1_p$ | $R^2_q$ | $IC_{50}$ (μM) |
|---|---|---|---|
| ABD430 | 2,4-Difluoro | 3-Chloro | 7 ± 2 |
| ABD68 | Unsubstituted | Unsubstituted | 22 ± 3 |

Biological Study 2

The biological activity of 1-(2',4'-dichloro-biphenyl-4-yl)-6-hydroxy-hexan-1-one (ABD328) can be compared to a range of related 2',4'-dichloro-biphenyl derivatives, wherein the group W has been varied, using the assays described previously. For example, $IC_{50}$ values were determined for several 2',4'-dichloro-biphenyl compounds using the Alamar Blue macrophage J774 viability assay described above. The results are summarised in the following table. These results demonstrate that the claimed variations on the W group give compounds with similar or improved potency in this assay. The results also demonstrate the importance of the conformation at the chiral centre.

TABLE 3

Alamar Blue Macrophage J774 Viability Assay

| Compound | W | $IC_{50}$ (μM) |
|---|---|---|
| ABD328 | —C(=O)— | 11 ± 3 |
| ABD468 | —C(=N—OH)— | 7 ± 2 |
| ABD300 | (R,S)—CH(OH)— | 8 ± 2 |
| ABD511 | (R)—CH(OH)— | 4 ± 2 |
| ABD513 | (S)—CH(OH)— | 11 ± 4 |

Biological Study 3

The effects of biphenyl ketones as orally active anti-resorptive agents were investigated in the mouse-ovariectomy bone loss model as described above.

Compounds ABD68, ABD328 and ABD355 (dosage 20 mg/kg, orally) were investigated in vivo using ovariectomy induced bone loss assessed using peripheral quantitative computed tomography, as described above.

The ovariectomy-induced bone loss data are illustrated in FIG. 1.

FIG. 1 is a bar graph showing percent changes in trabecular density, for: (a) Sham operation, no drug; (b) OVX operation, no drug; (c) OVX operation, ABD68 (20 mg/kg, orally); (d) OVX operation, ABD355 (20 mg/kg, orally); (e) OVX operation, ABD328 (20 mg/kg, orally). The graph shows that OVX causes a 34% decrease in trabecular bone density relative to the control group. The groups treated with ABD68 and ABD355 show 21% and 10% decreases respectively, whereas the group treated with ABD328 shows a 6% increase in trabecular bone density.

The data show that ABD328 is able to fully reverse the effects of ovariectomy-induced bone loss, and show that ABD328 is very effective at reversing the bone loss seen in this model for post-menopausal osteoporosis. The data also demonstrate that ABD68 and ABD355 are much less effective at reversing the effects of bone loss in this model. The data also demonstrate the superiority of ABD328 over known biphenyl ketones, such as ABD68 and ABD355, as an orally active anti-resorptive agent.

Biological Study 4

The oral absorption of several biphenyl ketones was investigated in a rat model as described previously.

Serum levels of compounds ABD328, ABD345 and ABD430 following oral dosage (10 mg/kg) over the course of 60 minutes were investigated in vivo in rats using an HPLC/UV detection system, as described above.

Figure 2:
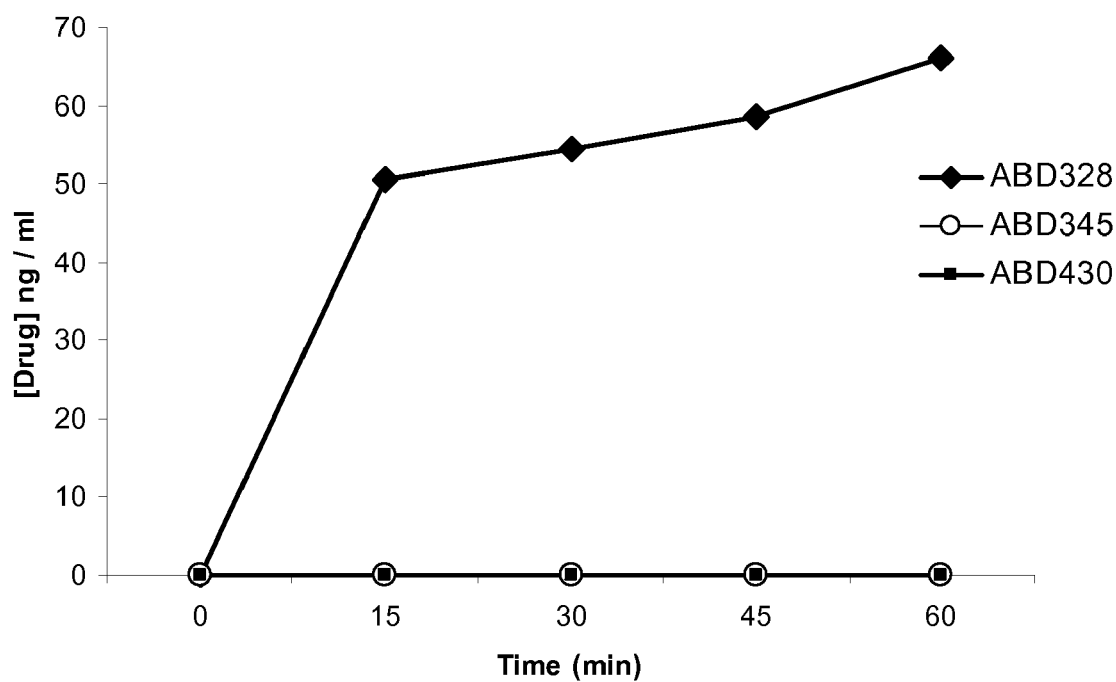
FIG. 2 is a graph showing blood serum levels (ng/mL) of ABD328 (♦), ABD345 (○) and ABD430 (■) as a function of time (minutes) after oral administration of the drug (10 mg/kg). The graph shows that ABD328 is well absorbed whereas ABD345 and ABD430 are not absorbed following oral dosage.

FIG. 2 is a graph showing blood serum levels (ng/mL) of ABD328 (♦), ABD345 (○) and ABD430 (■) as a function of time (minutes) after oral administration of the drug (10 mg/kg). The graph shows that ABD328 is well absorbed whereas ABD345 and ABD430 are not absorbed following oral dosage.

The data show that ABD328 is well absorbed following oral administration and has a good degree of metabolic stability, and is therefore ideal as an orally active drug. The data also demonstrate that ABD345 and ABD430 are either not absorbed following oral dosing, or else are very rapidly metabolized as to preclude their detection within 15 minutes. Therefore, the data highlights the exceptional properties of ABD328 in comparison to other members of the biphenyl ketone class.

Biological Study 5

The effect of ABD328 as an anti-inflammatory agent was investigated in the mouse collagen-induced arthritis model, as described above.

Compound ABD328 (dosage 10 mg/kg, i.p. or oral) was investigated in vivo using the collagen-induced arthritis model, assessed using joint inflammation severity scoring, as described above.

Figure 3:
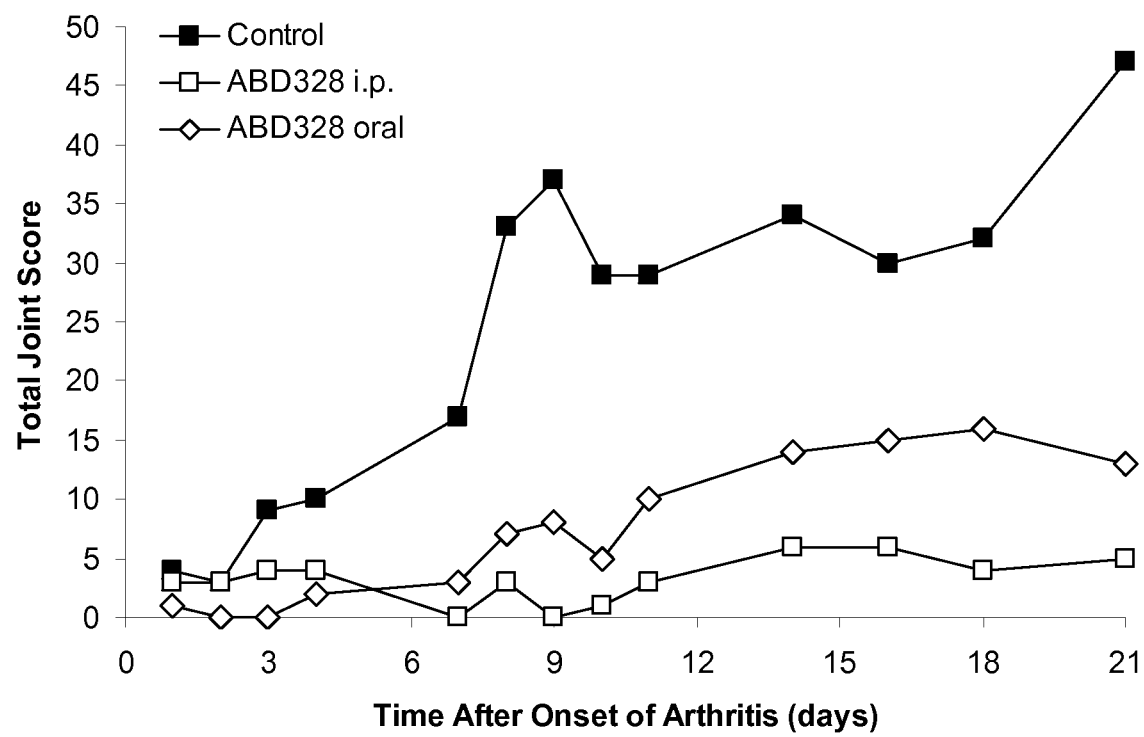
FIG. 3 is a graph showing the sum of the joint inflammation scores for each study group over a 21-day period following the first signs of inflammation in an arthritis model: (■) control group, no drug; (□) ABD328 (10 mg/kg/day, i.p.); (◇) ABD328 (10 mg/kg/day, orally); n=10 animals per group. The graph shows that the untreated study group has a total joint score of 47, whereas the group treated with ABD328 orally has a score of 13 and the group treated with ABD328 i.p. has a score of 5.

The collagen-induced arthritis data are illustrated in FIG. 3.

FIG. 3 is a graph showing the sum of the joint inflammation scores for each study group over a 21-day period following the first signs of inflammation in an arthritis model: (■) control group, no drug; (□) ABD328 (10 mg/kg/day, i.p.); (◊) ABD328 (10 mg/kg/day, orally); n=10 animals per group. The graph shows that the untreated study group has a total joint score of 47, whereas the group treated with ABD328 orally has a score of 13 and the group treated with ABD328 i.p. has a score of 5.

The data show that ABD328 is able to fully reverse the effects of collagen-induced arthritis, and show that ABD328 is very effective at preventing the inflammation seen in this model for arthritis, either by injection or as an orally active drug.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Baud V, Liu Z G, Bennett B, Suzuki N, Xia Y, Karin M, 1999, "Signaling by proinflammatory cytokines: oligomerization of TRAF2 and TRAF6 is sufficient for JNK and IKK activation and target gene induction via an amino-terminal effector domain", *Genes Dev.*, Vol. 13, pp. 1297-1308.

Brennan F M, Chantry D, Jackson A, Maini R, Feldmann M, 1989, "Inhibitory effect of TNF alpha antibodies on synovial cell interleukin-1 production in rheumatoid arthritis", *Lancet*, Vol. 2, pp. 244-247

Brennan F M, Feldmann M, 1996, "Cytokines in autoimmunity", *Curr. Olin. Immunol.*, Vol. 8, pp. 872-877.

Brennan F M, Gibbons D L, Mitchell T, Cope A P, Maini R N, Feldmann M, 1992, "Enhanced expression of tumor necrosis factor receptor mRNA and protein in mononuclear cells isolated from rheumatoid arthritis synovial joints", *Eur. J. Immunol.*, Vol. 22, pp. 1907-1912.

Corey E J, Shibata S, Bakshi R K, 1988, "An efficient and catalytically enantioselective route to (S)-(-)-Phenyloxirane," *J. Org. Chem.*, Vol. 53, pp. 2861-2863.

Elliott M J, Maini R N, Feldmann M, Kalden J R, Antoni C, Smolen J S, Leeb B, Breedveld F C, Macfarlane J D, Bijl H 1994, "Randomised double-blind comparison of chimeric monoclonal antibody to tumour necrosis factor alpha (cA2) versus placebo in rheumatoid arthritis", *Lancet*, Vol. 344, pp. 1105-1110.

Feldmann M, Brennan F M, Elliott M, Katsikis P, Maini R N, 1994, "TNF alpha as a therapeutic target in rheumatoid arthritis," *Circ. Shock*, Vol. 43, pp. 179-184.

Feldmann M, Brennan F M, Foxwell B M, Maini R N, 2001, "The role of TNF alpha and IL-1 in rheumatoid arthritis," *Curr. Dir. Autoimmun.*, Vol. 3, pp. 188-199.

Feldmann M, Brennan F M, Maini R N, 1996, "Rheumatoid arthritis", *Cell*, Vol. 85, pp. 307-310.

Firestein G S, 1996, "Invasive fibroblast-like synoviocytes in rheumatoid arthritis. Passive responders or transformed aggressors?", *Arthritis Rheum.*, Vol. 39, pp. 1781-1790.

Firestein G S, 2005 "Immunologic mechanisms in the pathogenesis of rheumatoid arthritis", *J. Clin. Rheumatol.*, Vol. 11. pp. S39-S44.

Firestein G S, Manning A M, 1999, "Signal transduction and transcription factors in rheumatic disease", *Arthritis Rheum.*, Vol. 42, pp. 609-621.

Gottlieb A B, 2005, "Psoriasis: Emerging Therapeutic Strategies", *Nat. Rev. Drug Disc.*, Vol. 4, pp. 19-34.

Greig I R, Idris A I, Ralston S H and van't Hof R J, "Ketones and reduced ketones as therapeutic agents for the treatment of bone conditions", published international patent application publication number WO 2004/09858.

Jimi E, Aoki K, Saito H, D'Acquisto F, May M J, Nakamura I, Sudo T, Kojima T, Okamoto F, Fukushima H, Okabe K, Ohya K, Ghosh S, 2004, "Selective inhibition of NF-kappa B blocks osteoclastogenesis and prevents inflammatory bone destruction in vivo", *Nat. Med.*, Vol. 10, pp. 617-624.

Joosten L A, Helsen M M, van de Loo F A, van den Berg W B, 1996, "Anticytokine treatment of established type II collagen-induced arthritis in DBA/1 mice. A comparative study using anti-TNF alpha, anti-IL-1 alpha/beta, and IL-1Ra," *Arthritis Rheum.*, Vol. 39, pp. 797-809.

Klareskog L, Gaubitz M, Rodriguez-Valverde V, Malaise M, Dougados M, Wajdula J, 2006, "A long-term, open-label trial of the safety and efficacy of etanercept (Enbrel) in patients with rheumatoid arthritis not treated with other disease-modifying antirheumatic drugs", *Ann. Rheum. Dis.*, Vol. 65, pp. 1578-1584.

Klareskog L, Padyukov L, Lorentzen J, Alfredsson L, 2006, "Mechanisms of disease: Genetic susceptibility and environmental triggers in the development of rheumatoid arthritis," *Nat. Clin. Pract. Rheumatol.*, Vol. 2, pp. 425-433.

Korzenik J R and Podolsky D K, 2006, "Evolving knowledge and therapy of inflammatory bowel disease," *Nat. Rev. Drug Disc.*, Vol. 5, pp. 197-209.

Liu Z G, 2005, "Molecular mechanism of TNF signaling and beyond," *Cell Res.*, Vol. 15, pp. 24-27.

Luckman S P, Coxon F P, Ebetino F H, Russell R G, Rogers M J, 1998, "Heterocycle-containing bisphosphonates cause apoptosis and inhibit bone resorption by preventing protein prenylation: evidence from structure-activity relationships in J774 macrophages," *J. Bone Miner. Res.*, Vol. 13, pp. 1668-1678.

McInnes I B, Gracie J A, 2005, "Targeting cytokines beyond tumor necrosis factor-alpha and interleukin-1 in rheumatoid arthritis", *Curr. Pain Headache Rep.*, Vol. 9, pp. 405-411.

Mount C and Featherstone J, 2005, "Rheumatoid arthritis market", *Nat. Rev. Drug Disc.*, Vol. 2, pp. 11-12.

Nociari, M. N., et al., 1998, "A Novel one-step, highly sensitive fluorimetric assay to evaluate cell-mediated cytotoxicity", *Journal of Immunological Methods*, Vol. 213, pp. 157-167.

Ramachandran P V, Gong B. Brown H C, 1995, "Chiral synthesis via organoboranes", *J. Org. Chem.*, Vol. 60, pp. 41-46.

Roodman G D, 2006, "Regulation of osteoclast differentiation", *Ann. N.Y. Acad. Sci.*, Vol. 1068, pp. 100-109.

Smolen J S and Steiner G, 2003, "Therapeutic Strategies for Rheumatoid Arthritis", *Nat. Rev. Drug Disc.*, Vol. 2, pp. 473-488.

Tanaka S, Nakamura I, Inoue J, Oda H, Nakamura K, 2003, 2Signal transduction pathways regulating osteoclast differentiation and function," *J. Bone Miner. Metab.*, Vol. 21, pp. 123-133.

van den Berg W B, 2002, "Is there a rationale for combined TNF and IL-1 blocking in arthritis?", *Clin. Exp. Rheumatol.*, Vol. 20, pp. S21-S25.

van den Berg W B, Bresnihan B, 1999, "Pathogenesis of joint damage in rheumatoid arthritis: evidence of a dominant role for interleukin-I", *Baillieres Best Pract. Res. Clin. Rheumatol.*, Vol. 13, pp. 577-597.

Weissmann G, 2006, "The pathogenesis of rheumatoid arthritis," *Bull. Hosp. Jt. Dis.*, Vol. 64, pp. 12-15.

Ziff M, 1990, "Rheumatoid arthritis—it's present and future", *J. Rheumatol.*, Vol. 17, pp. 127-133.

The invention claimed is:

1. A compound selected from compounds of the following formula and pharmaceutically acceptable salts thereof:

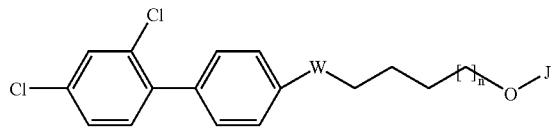

wherein:
n is independently 1, 2, 3, or 4;
W is independently —C(=O)—, —CH(OH)—, or —C(=NOR$^{OX}$)—;
R$^{OX}$ is independently —H or C$_{1-3}$alkyl;
J is independently:
—H,
—R$^{E1}$,
—C(=O)—R$^{E2}$,
—C(=O)—O—R$^{E3}$,
—C(=O)—O—S(=O)$_2$OR$^{E4}$,
—C(=O)—(CH$_2$)$_n$—C(=O)OR$^{E5}$,
—C(=O)—(CH$_2$)$_n$—NR$^{NE1}$R$^{NE2}$,
—C(=O)—(CH$_2$)$_n$—NR$^{NE3}$—C(=O)R$^{E6}$,
—C(=O)—(CH$_2$)$_n$—C(=O)—NR$^{NE4}$R$^{NE5}$, or
—P(=O)(OR$^{E7}$)(OR$^{E8}$);
wherein each of R$^{E1}$, R$^{E2}$, R$^{E3}$, R$^{E4}$, R$^{E5}$, R$^{E6}$ and R$^{E7}$ is independently:
—H, C$_{1-3}$alkyl, -Ph, or —CH$_2$-Ph.

2. A compound according to claim 1, wherein n is independently 2 or 3.

3. A compound according to claim 1, wherein W is independently —C(=O)—.

4. A compound according to claim 1, wherein W is independently —CH(OH)—.

5. A compound according to claim 1, wherein W is independently —C(=NOR$^{OX}$)—.

6. A compound according to claim 1, wherein J is independently —H, —R$^{E1}$, or —C(=O)—R$^{E2}$.

7. A compound according to claim 1, wherein J is independently —H.

8. A compound according to claim 1, wherein each of R$^{E1}$, R$^{E2}$, R$^{E3}$, R$^{E4}$, R$^{E5}$, R$^{E6}$, and R$^{E7}$, if present, is independently —H or C$_{1-3}$alkyl.

9. A compound according to claim 1, selected from compounds of the following formulae and pharmaceutically acceptable salts thereof:

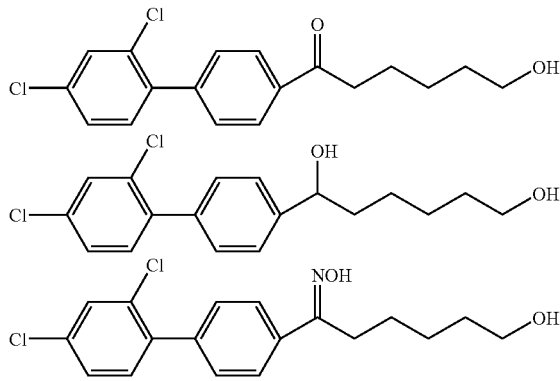

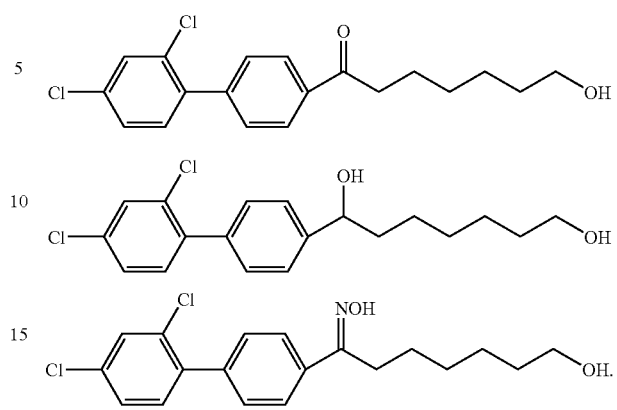

10. A compound selected from a compound of the following formula and pharmaceutically acceptable salts thereof:

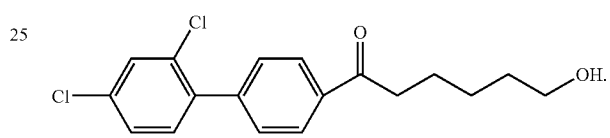

11. A compound according to claim 10, of the following formula:

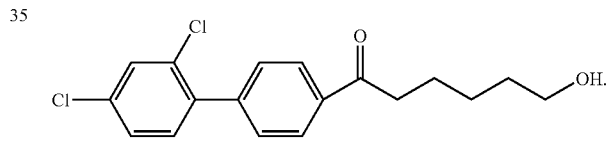

12. A compound selected from compounds of the following formula and pharmaceutically acceptable salts thereof:

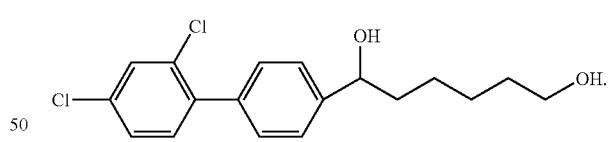

13. A compound according to claim 12, selected from a compound of the following formula and pharmaceutically acceptable salts thereof:

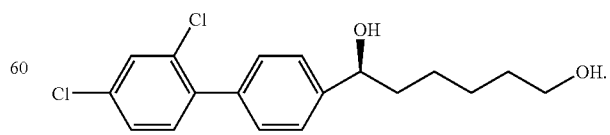

14. A compound according to claim 12, selected from a compound of the following formula and pharmaceutically acceptable salts thereof:

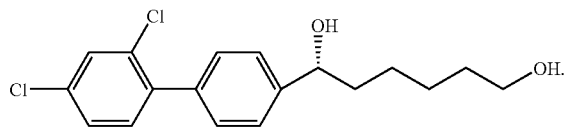

15. A compound according to claim 12, selected from compounds of the following formula:

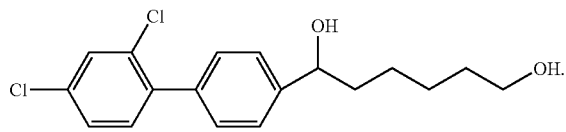

16. A compound according to claim 12, of the following formula:

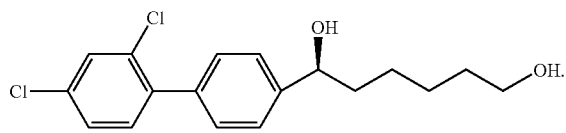

17. A compound according to claim 12, of the following formula:

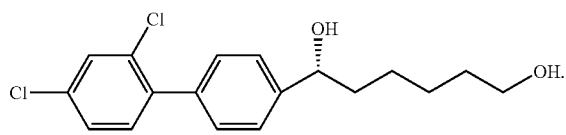

18. A pharmaceutical composition comprising a compound according to claim 1 and a pharmaceutically acceptable carrier or diluent.

19. A method of making a pharmaceutical composition comprising admixing or otherwise combining a compound according to claim 1 and a pharmaceutically acceptable carrier or diluent.

20. A method of inhibiting an inflammatory response, in vitro or in vivo, comprising contacting an immune system component with an effective amount of a compound according to claim 1.

21. A method of inhibiting osteoclast survival, formation, and/or activity, in vitro or in vivo, comprising contacting an osteoclast with an effective amount of a compound according to claim 1.

22. A method of inhibiting bone resorption, in vitro or in vivo, comprising contacting cells in the bone microenvironment with a therapeutically-effective amount of a compound according to claim 1.

23. A method of treatment of:

an inflammatory disorder or an autoimmune disorder; a disorder associated with inflammation and/or activation of the immune system; a disorder mediated by excessive and/or inappropriate and/or prolonged activation of the immune system; inflammation; a disorder associated with inflammation or activation of the immune system; rheumatoid arthritis; psoriasis; psoriatic arthritis; ankylosing spondylitis; inflammatory bowel disease; an immune response leading to organ or graft rejection following transplant; a tumor which over expresses TNFα, IL-1, or RANKL or in which inhibition of TNFα, IL-1, or RANKL facilitates or improves the action of cytotoxic tumoricidal agents; a disorder mediated by osteoclasts; a disorder characterised by excessive bone resorption; bone loss; bone loss associated with inflammation; bone loss not associated with inflammation; bone loss associated with excessive osteoclast activation; joint destruction; joint destruction associated with inflammation; joint destruction associated with excessive osteoclast activation; bone loss associated with rheumatoid arthritis, osteoporosis, cancer associated bone disease, or Paget's disease of bone; rheumatoid arthritis, osteoporosis, cancer associated bone disease, or Paget's disease of bone; neoplasia of bones; hypercalcaemia caused by conditions associated with increased bone resorption; aseptic loosening of prosthetic implants; or osteopetrosis, osteoarthritis, or ectopic bone formation;

said method comprising administering to a patient in need of treatment and/or prevention a therapeutically effective amount of a compound according to claim 1.

24. A method according to claim 23, wherein said administering is orally administering.

* * * * *